(12) United States Patent
Jiang et al.

(10) Patent No.: US 11,299,754 B2
(45) Date of Patent: *Apr. 12, 2022

(54) GENE TARGETING METHOD

(71) Applicant: HANGZHOU GENEKINE BIOTECH CO., LTD, Zhejiang (CN)

(72) Inventors: Youwei Jiang, Zhejiang (CN); Yunfei Li, Zhejiang (CN)

(73) Assignee: HANGZHOU GENEKINE BIOTECH CO., LTD, Zhejiang (CN)

( * ) Notice: Subject to any disclaimer, the term of this patent is extended or adjusted under 35 U.S.C. 154(b) by 864 days.

This patent is subject to a terminal disclaimer.

(21) Appl. No.: 15/570,517

(22) PCT Filed: Apr. 29, 2016

(86) PCT No.: PCT/CN2016/080785
§ 371 (c)(1),
(2) Date: Oct. 30, 2017

(87) PCT Pub. No.: WO2016/173555
PCT Pub. Date: Nov. 3, 2016

(65) Prior Publication Data
US 2018/0355381 A1    Dec. 13, 2018

(30) Foreign Application Priority Data

Apr. 30, 2015  (CN) .......................... 201510220631.9

(51) Int. Cl.
| | | |
|---|---|---|
| C12N 15/90 | (2006.01) | |
| C12N 15/11 | (2006.01) | |
| C12N 1/16 | (2006.01) | |
| C12P 21/00 | (2006.01) | |
| C12N 9/12 | (2006.01) | |

(52) U.S. Cl.
CPC ............ *C12N 15/905* (2013.01); *C12N 1/16* (2013.01); *C12N 9/1241* (2013.01); *C12N 15/11* (2013.01); *C12N 15/902* (2013.01); *C12P 21/00* (2013.01); *C12N 2800/30* (2013.01)

(58) Field of Classification Search
None
See application file for complete search history.

(56) References Cited

U.S. PATENT DOCUMENTS

| | | | | |
|---|---|---|---|---|
| 4,959,317 A | * | 9/1990 | Sauer ..................... | C12N 15/00 435/254.2 |
| 2015/0267212 A1 | * | 9/2015 | Gehlsen ........... | C12Y 302/0113 435/254.23 |
| 2017/0240869 A1 | * | 8/2017 | Soucaille ....... | C12Y 203/01016 |

FOREIGN PATENT DOCUMENTS

| | | |
|---|---|---|
| CN | 1844401 | 10/2006 |
| CN | 101195809 A | 6/2008 |
| CN | 101440352 | 5/2009 |

OTHER PUBLICATIONS

Lepage et al., "Animal Models for Disease" 129 Methods in Molecular Medicine 41-67 (Year: 2006).*
Z. Chen et al., "Enhancement of the Gene Targeting Efficiency of Non-Conventional Yeasts by Increasing Genetic Redundance," PLOS ONE, vol. 8, No. 3 (2013), 9 pages.
International Search Report for international appl. No. PCT/CN2016/080785, dated Aug. 4, 2016 (4 pages, including English translation).
Heaney Jason D. et al.: "Tissue-specific expression of a BAC transgene targeted to the Hprt locus in mouse embryonic stem cells", Genomics, 2004, vol. 83, No. 6 , pp. 1072-1082.
Hernandez Diana et al.: "Deletion of genes from the mouse genome using Cre/loxP technology", Methods in Molecular Biology (Clifton, N.J.) 2006, vol. 320, pp. 307-319.
Johansson B. and Hahn-Hagerdal B.: "Overproduction of pentose phosphate pathway enzymes using a new CRE-/oxP expression vector for repeated genomic integration in *Saccharomyces cerevisiae*", Yeast, John Wiley & Sons L To, GB, vol. 19, No. 3, Feb. 1, 2002, pp. 225-231.
Stephan J. et al.: "Consecutive gene deletions in *Mycobacterium smegmatis* using the yeast FLP recombinase", Gene, Elsevier, Amsterdam, NL, vol. 343, No. 1, Dec. 8, 2004, pp. 181-190.
The extended European Search Report issued in corresponding European application No. 16785983.4, dated Oct. 26, 2018, 9 pages provided.
Office Action issued in corresponding Chinese application No. 201510220631.9, dated Jul. 1, 2019, with machine translation, 11 pages provided.
Search Report issued in in corresponding Chinese application No. 201510220631.9, dated Jun. 21, 2019, with machine translation, 3 pages provided.
Chen et al., "Enhancement of the gene targeting efficiency of non-conventional yeasts by increasing genetic redundancy", PLOS ONE, vol. 8, Issue 3, Mar. 2013, 11 pages provided.
Choi et al., "Use of combinatorial genetic libraries to humanize N-linked glycosylation in the yeast Pichia pastoris", PNAS, vol. 100, No. 9, Apr. 29, 2003, 6 pages provided.
Nancy L. Craig, "The mechanism of conservative site-specific recombination", Annu. Rev. Genet, available at www.annualreviews.org, Access provided Apr. 19, 2020, 29 pages provided.

(Continued)

*Primary Examiner* — Nancy J Leith
(74) *Attorney, Agent, or Firm* — Hamre, Schumann, Mueller & Larson, P.C.

(57) ABSTRACT

Provided are a novel two-step gene targeting method and a nucleotide construct for gene targeting. The method can improve the gene targeting efficiency and accurately identify a target gene knock-out mutant. The method of the present invention comprises: firstly, efficiently replacing a target gene in a genome with a targeting box by homologous recombination, the targeting box consisting of a target gene activity variant, a marker gene and site-specific recombination sites; and secondly, resecting the targeting box by recombinase, leaving a site-specific recombination site on the target gene to generate a target gene knock-out mutant, and removing a recombinase expression vector from the knock-out mutant by using a counter selection marker in the recombinase expression vector.

17 Claims, 11 Drawing Sheets

Specification includes a Sequence Listing.

(56) References Cited

OTHER PUBLICATIONS

Klinner et al., Genetic aspects of targeted insertion mutagenesis in yeasts, FEMS Microbiology Reviews, vol. 28, Issue 2, May 1, 2004, 23 pages provided.

Näätsaari et al., Deletion of the Pichia pastoris KU70 homologue facilitates platform strain generation for gene expression and synthetic biology, PLOS ONE, vol. 7, Issue 6, Jun. 2012, 25 pages provided.

Nett et al., Cloning and disruption of the Pichia pastoris ARG1, ARG2, ARG3, HIS1, HIS2, HIS5, HIS6 genes and their use as auxotrophic markers, John Wiley & Sons, Ltd., Yeast 2005, 10 pages provided.

Pâques et al., "Multiple pathways of recombination induced by double-strand breaks in *Saccharomyces cerevisiae*", Microbiology and Molecular Biology Reviews, Jun. 1999, 56 pages provided.

Wahls et al., "Meiotic Recombination Hotspots of Fission Yeast are Directed to Loci that Express Non-Coding RNA", PLOS ONE, vol. 3, Issue 8, Aug. 2008, 8 pages provided.

Yang et al., "mazF as a counter-selectable marker for unmarked genetic modification of Pichia pastoris", Method for genetic modification of Pichia Pastoris, FEMS Yeast Res 9, 2009, 10 pages provided.

Examination Report issued in European Application No. 16 785 983.4, dated Nov. 29, 2021 (7 pages).

Lepage David F. et al.: "Animal models for disease: knockout, knock-in, and conditional mutant mice", Methods in Molecular Medicine, Humana Press, vol. 129, Jan. 1, 2006, pp. 41-67, ISSN: 1543-1894.

Anonymous: "Targeting Vector Design", Oct. 29, 2007, Retrieved from the Internet: URL: http://ko.cwru.edu/info/targvectdesign.html, (5 pages).

Ray Manas K. et al.: "The Cre-loxP system: a versatile tool for targeting genes in a cell- and stage-specific manner", Cell Transplantation, vol. 9, No. 6, Nov. 1, 2000, pp. 805-815.

* cited by examiner

GENE TARGETING METHOD

INCORPORATION BY REFERENCE OF MATERIAL IN ASCII TEXT FILE

This application incorporates by reference the Sequence Listing contained in the following ASCII text files submitted herewith:
 a) Filename: SequenceListing_0135.txt, created Oct. 30, 2017, 23,079 bytes in size; and
 b) Filename: seq_listing_0135USWO.txt, created on Apr. 16, 2018, 21,785 bytes in size.

TECHNICAL FIELD

The present invention relates to the field of biotechnology; in particular, to a novel two-step gene targeting method and to a nucleotide construct for using in the method.

BACKGROUND

Cell transformation means that an exogenous DNA is introduced into cells. Permanent transformation is usually the result of integration of the exogenous DNA in chromosome DNA. Gene targeting is a process for chromosomal integration of the exogenous DNA at a genetic locus, which typically cause the gene at the target locus to be modified, replaced or duplicated. Gene targeting is a process common to all life.

Gene targeting is mediated via the repair of DNA double-strand breaks (DSBs). Such repair occurs via two distinctively different molecular mechanisms: homologous recombination (HR) pathway and non-homologous end-joining (NHEJ) pathway. In cells, HR is an accurate pathway that repairs double-strand breaks by using the information from homologous sequences. In HR gene targeting, an exogenous DNA fragment, usually a selectable marker gene is precisely integrated at its homologous genome counter-part through homologous sequences at each end. On the contrary, in non-homologous end-joining pathway, an exogenous DNA fragment with selectable marker gene will randomly integrate at nonhomologous chromosomal sites. When the exogenous DNA fragment is transformed into cells, HR competes with NHEJ pathways (Paques and Haber 1999, Microbiology and Molecular Biology Reviews, 63: 349-404). Therefore, the efficiency of site-specific gene targeting is determined by the relative strength between HR and NHEJ pathways.

Gene targeting is an important tool for modifying yeast and studying molecular genetics. Conventional yeast *Saccharomyces cerevisiae* and fission yeast, *Schizosaccharomyces pombe*, have very efficient gene targeting systems. In *S. cerevisiae*, the frequency of gene replacement events can be as many as 95% of the total tranformants when the targeting fragments are 30 to 45 bp (Paques and Haber 1999, Microbiology and Molecular Biology Reviews, 63: 349-404). However, the gene targeting efficiencies in methylotrophic yeast *Pichia pastoris* and other "non-conventional" yeasts, such as *Hansenula polymorpha, Yarrowia lipolytica, Pichia stipitis* and *Kluyveromyces lactis* can be extremely low. The frequency of gene replacement events is highly dependent on the length of homologous sequence in the targeting fragment. It can be less than 0.1% when the targeting homologous sequences are less than 500 bp, but it can be greater than 50% for some target sites when extensive 1 kb targeting homologous sequences are used (Klinner U, et al (2004) *Fems Microbiology Reviews* 28: 201-223; Gregg J M (2010) *Pichia* Protocols, Second edition. Totowa, N.J.: Humanna Press).

Random gene targeting in "non-conventional" yeasts seems to be dominant by NHEJ pathway. NHEJ pathway in *P. pastoris* is highly dependent on the Ku70p/Ku80p protein heterodimer to recognize and bind to DNA ends. Deletion of the Ku70p in the heterodimer can strongly reduce the random integration and significantly increase the homologous recombination efficiency in *P. pastoris*. Although inactivation of KU70 enables the quick construction of precise site directed genomic disruption, the ku70 deletion strain was observed to express decelerated growth, cause unknown metabolic changes, and have possible defects in DNA-repairing process. Therefore, it limits the use of the ku70 deletion strain in gene targeting (naatsaari, et al 2012, PLoS ONE, 7: e39720).

The non-specific process of NHEJ is also dominant in filamentous fungi and higher eukaryotic organisms. The strategy to reduce the random gene targeting by deleting components of NHEJ-pathway has applied to these organisms, including fungi like *Aspergillus* sp., *Magnaporthe grisea, Neurospora* sp., yeasts like *Kluyveromyces lactis, candida glabrata, Saccharomyces cerevisiae, Pachia pastoris*, and mammalian CHO cells (naatsaari, et al 2012, PLoS ONE, 7: e39720).

Besides the random gene targeting by NHEJ pathway, the efficiency of homologous integration in strains with the same genetic background can be locus dependent. For example, the disruptions of ARG1, ARG2, ARG3, HIS1, HIS2, HIS5, and HIS6 in *P. pastoris* GS115 strain occur at a high frequencies of 44-90% when the lengths of targeting fragments are range within 200 to 900 bp (Nett, et al (2005) Yeast 22: 295-304). But the deletion of OCH1 and SGS1 in *P. pastoris* is significantly low efficient at a frequency of <1% when ~1 kb or more regions of homology are used (Choi, et al. (2003) Proc Natl Acad Sci USA 100: 5022-5027; Chen, et al. (2013) PLoS ONE 8(3): e57952). The molecular mechanism for this locus dependent phenomenon is not well understood. One possible reason is that there are hotspot regions along each chromosome and homologous recombination is positioned preferentially at hotspots (Wahls et al. Plos One 3:e2887).

Loss of gene function can be another important factor to cause the low efficiency of gene targeting. The disruption of a gene with important physiological function usually leads to great loss of cellular fitness and delayed appearance of disruption transformants. Therefore, it is a great challenge to identify a small number of target gene disruption transformants from the majority of random integration transformants, which possess normal target gene function. For example, extensive screening can hardly identify OCH1 disruption transformants in *P. pastoris*. A method of increasing the genetic redundancy has been utilized to improve the fitness of OCH1 disruption transformants thereby enhance the efficiency of OCH1 gene targeting in *P. pastoris* (Chen, et al. (2013) PLoS ONE 8(3): e57952). However, in this method, the removal of redundant gene still can cause the loss of cellular fitness and result in the failure to identify the target gene disruption transformants.

In summary, the low efficiency of homologous recombination and intensive screening to identify disruption mutants are two major obstacles that constrain the application of gene targeting technology. Therefore, there is an urgent need in the art for a method to improve the gene targeting efficiency and simplify the identification of disruption strains.

SUMMARY OF THE INVENTION

The purpose of the present invention is to provide a method for enhancing gene targeting efficiency and simplifying the identification of disrupted strains and technical means used in the method.

In the first aspect, a nucleotide construct for gene targeting is provided in the present invention, with the following structures:

5'-$A_1$-$B_1$-$C_1$-$C_2$-X-$B_2$-$A_2$-3';

5'-$A_1$-$B_1$-X-$C_1$-$C_2$-$B_2$-$A_2$-3';

5'-$A_1$-$B_1$-$C_1$-X-$B_2$-$C_2$-$A_2$-3'; or

5'-$A_1$-$B_1$-X-$C_1$-$B_2$-$C_2$-$A_2$-3'

Wherein, $A_1$, $A_2$ are homologous sequences;

$B_1$, $B_2$ are site-specific recombination sites;

$C_1$, $C_2$ are marker genes and can not be absent at the same time;

X is target gene active variant;

the target gene active variant possesses a functional activity of the target gene.

In a preferred embodiment, the target gene active variant has 30-100%, preferably 65-100%, most preferably 95-100% sequence identity to the target gene, and has the functional activity of the target gene.

In a preferred embodiment, the target gene active variant is identical with the target gene.

In a specific embodiment, the site-specific recombination site is loxP site or FRT site, and the like; preferably, loxP site.

In a specific embodiment, the target gene active variant can further comprise promoter and/or terminator.

In a preferred embodiment, $C_1$, $C_2$ can be the same or different; preferably, ADE1, BLA or Shble (Zeocin$^r$) gene.

In a preferred embodiment, the marker gene can be selection markers, screening markers and molecular markers.

In a preferred embodiment, the nucleotide construct may be circular or linear.

In a preferred embodiment, there can be a linker between the parts of the nucleotide construct.

In a preferred embodiment, the homologous sequence is 600-2000, preferably 700-1500, most preferably 800-1000 bp in length.

In a preferred embodiment, the disruption efficiency for the target gene used in gene targeting is lower than 3% by using conventional targeting methods.

In a preferred embodiment, the target gene used in gene targeting is OCH1, ARG4 gene.

In the second aspect, a composition used for gene targeting is provided in the present invention, wherein the composition comprises the nucleotide construct according to the first aspect of the present invention and expression vector for recombinase.

In a specific embodiment, the recombinase is Cre recombinase or Flp recombinase; preferably, Cre recombinase.

In a preferred embodiment, the expression vector for recombinase further comprises counter-selection marker.

In the third aspect, a host cell is provided in the present invention, comprising the nucleotide construct according to the first aspect of the present invention.

In a specific embodiment, the host cell is yeast.

In a preferred embodiment, the yeast is *Saccharomyces cerevisiae, Schizosaccharomyces pombe, Pichia pastoris, Hansenula polymorpha, Yarrowia lipolytica, Pichia stipitis* and *Kluyveromyces lactis*.

In a preferred embodiment, the yeast is *Pichia pastoris, Hansenula polymorpha, Yarrowia lipolytica, Pichia stipitis* and *Kluyveromyces lactis*.

In a preferred embodiment, the host cell further comprises an expression vector for recombinase.

In a preferred embodiment, the recombinase is Cre recombinase or Flp recombinase; preferably, Cre recombinase.

In a preferred embodiment, the expression vector for recombinase further comprises a counter-selection marker gene.

In the fourth aspect, a method for gene targeting is provided in the present invention, comprising:

a) constructing the nucleotide construct according to the first aspect of the present invention;

b) introducing the nucleotide construct obtained in step a) into a cell, thereby replacing a target gene in genome with the nucleotide construct via homogeneous recombination;

c) excising the nucleotide construct by recombinase, thereby leaving behind one site-specific recombination site on the target gene and yielding a mutant of the target gene.

In a specific embodiment, the method further comprises removing the expression vector for recombinase by using the counter-selection marker gene on the expression vector for recombinase.

In a preferred embodiment, the disruption efficiency for the target gene used in gene targeting is lower than 3% by using conventional targeting methods.

In a preferred embodiment, the target gene used in gene targeting is OCH1, ARG4 gene.

In the fifth aspect, a method for engineering a strain is provided, comprising:

a) constructing the nucleotide construct according to the first aspect of the present invention;

b) introducing the nucleotide construct obtained in step a) into a strain to be engineered, thereby replacing a target gene in genome of the strain to be engineered with the nucleotide construct via homogeneous recombination;

c) introducing an expression vector for recombinase into the strain to be engineered, excising the nucleotide construct by expressed recombinase, thereby leaving behind one site-specific recombination site on the target gene and yielding a target gene disruption mutant.

In a specific embodiment, the method further comprises removing the expression vector for recombinase by using the counter-selection marker gene on the expression vector for recombinase.

In a preferred embodiment, the method further comprises a step of screening the engineered strain.

In the sixth aspect, use of a strain engineered by the method according to the fifth aspect of the present invention is provided in the present invention, wherein the strain is used for producing recombinant proteins, metabolites and used in biocatalytic reaction.

In a preferred embodiment, the glycosylation pattern in the recombinant protein is altered.

In a preferred embodiment, the use for producing metabolites means increasing the yield of isobutanol by knocking out LPD1 gene in yeast to eliminate the metabolic competitive route, and facilitating efficient production of L-lactic acid by knocking out PDC1 gene in a yeast to alter the alcoholic fermentation pathway in yeast.

In a preferred embodiment, the use in bio-catalysis means enhancing biocatalytic ability of yeast and increasing the conversion efficiency of glucose to phenylethanol by knocking out ARO8 gene in yeast.

It should be understood that in the present invention, the technical features specifically mentioned above and below (such as in the Examples) can be combined with each other, thereby constituting a new or preferred technical solution which needs not be individually described.

MODE FOR CARRYING OUT THE INVENTION

Figure 1:
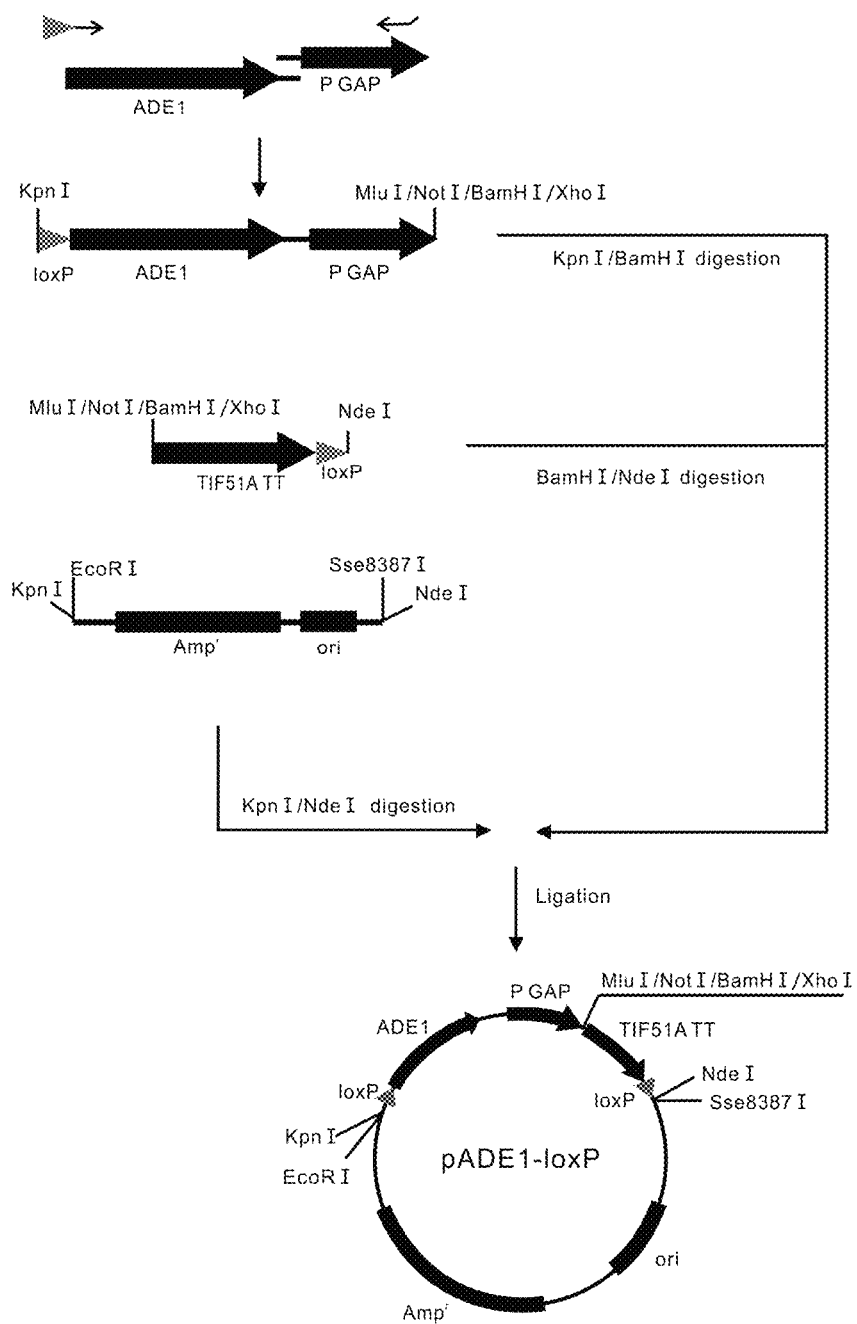
FIG. 1 depicts a scheme to construct pADE1-loxP vector. Vector components are not drawn to scale.

Upon extensive and deep study, the inventors have unexpectedly developed a two-step gene targeting method, and by such method, gene targeting efficiency can be enhanced and the identification of disruption mutants can be simplified. Based on the above results, the present invention was completed.

To overcome these obstacles, a two-step gene targeting method was developed in the present invention to enhance gene targeting efficiency and simplify the identification of disruption mutants. Firstly, the target locus in genome is replaced by homologous recombination at high frequency with a targeting cassette consisting of target gene active variant, selectable marker and site-specific recombination sites. Secondly, the targeting cassette is excised by a recombinase to leave behind one site-specific recombination site on the target locus and yield gene disruption mutants. Meanwhile, the excision of marker gene results in colony phenotype change and facilitates the precise identification of disruption mutants, which have lost cellular fitness and grown slowly in a small number. The method of the invention exploits homologous recombination processes that endogenous in the cells of all organisms, thus any gene of organisms can be disrupted by the method. The method can be widely used to create precise modifications in the genome of organisms as a tool for synthetic biology, metabolic engineering, systems biology, genetic studies, and biotechnology industry.

The present invention relates to methods and compositions for carrying out two-step gene targeting. The following terms are used herein according to the following definitions.

As used herein, the term "mutant strain" refers to a mutant obtained by completely or partially knocking out a gene in a genome; in particular, it means a knock-out mutant obtained by disruption of the gene by the gene targeting method of the present invention, especially a gene which is difficult to be disrupted by a conventional method.

"Gene targeting" is a process for chromosomal integration of an exogenous DNA at a genetic locus, which typically results in the gene at the target locus to be modified, replaced or duplicated. It is a mechanism common to all life.

Ends-in and ends-out refer to the two different arrangements of exogenous DNA that can be use for integration into the genome via homologous recombination. In gene targeting by ends-in recombination, the ends of linear exogenous DNA point toward each other when paired with a region of homology in genome locus, and integrate the DNA in the genome by single cross-over recombination (roll in). However, after recombination, exogenous DNA may be excised via homologous recombination between repeat sequences, and the initial wild-type state of the target gene can be restored due to the resulted repeating sequences of the same direction. In gene targeting by ends-out recombination, the ends of linear exogenous DNA point away from each other when paired with the homologous target in genome locus, and insert the DNA into the genome by double cross-over recombination between the terminal targeting flanks and the homologous chromosomal host genome sequence. Ends-out targeting is frequently used in mice and yeast, because it gives a straightforward route to replace or delete a target locus. However, ends-out events are less efficient than ends-in events. (Paques and Haber 1999, Microbiology and Molecular Biology Reviews, 63: 349-404). In the present invention, gene targeting refers to the ends-out double cross-over recombination, unless it is specifically indicated as ends-in targeting by single cross-over (roll-in).

"Cell" or "organism" is the term used for the organism in which gene targeting of the invention is carried out.

"Cell transformation" means an exogenous DNA is introduced into cells. It usually refers to a process of integration of the exogenous DNA in chromosome genome or introduction of self-replicated plasmid.

"Target gene" refers to the gene or DNA segment subject to alteration by the gene targeting method of the present invention. The target gene can be either any DNA segment in the genome of a host, or an exogenous DNA previously introduced into the organism, including but not limited to a polypeptide coding region, open reading frame (ORF), control region, intron, exon, or portion thereof.

"Target gene active variant" is a DNA segment which may be naturally occurring, or a fragment, variant, or derivative thereof. It can also be any sort of genetic change, including substitution of one segment for another, insertion and deletion of nucleotide, synthetic polynucleotide, and combinations thereof, which provides a functional activity in a manner similar to the wild type gene. The target gene active variant is a gene having a function of a target gene, and the sequence thereof may be the same as the target gene or may have certain changes as long as it has the same function as the target gene. In other embodiments, genes from other species having the same function may also be selected. For example, target genes from *Pichia pastoris* are used in Examples of the present invention, however, a skilled person in the art can reasonably expect that, based on the teachings of the present invention and the prior art, genes from other species, such as *Saccharomyces cerevisiae*, can also be used as target gene variants of the present invention.

The numbering of the nucleotide for the 5'- and 3'-regions refers to the respective start codon of the open reading frame (ORF) as nucleotides 1-3 (5' upstream area numbered with "−") and the respective stop codon as nucleotides+1 to +3 (3' downstream area numbered with "+").

"Marker" represents a gene or sequence whose presence or absence provides a detectable phenotype of the organism. These markers may be auxotrophic markers, resistance markers, and color markers. Various types of markers include, but not limited to, selection markers, screening markers and molecular markers.

Many loci in genome of organisms are difficult for gene targeting. The low efficiency of homologous recombination and intensive screening to identify disruption transformants are two major obstacles that constrain the application of gene targeting technology.

In accordance with this aspect thereof, a two-step gene targeting method is developed in the present invention to enhance gene targeting efficiency and facilitate the precise identification of disruption mutants.

First, the target locus in genome is replaced with a targeting cassette consisting of target gene active variant, marker gene and site-specific recombination sites. Thus, the cells of gene replacement transformants keep the similar biological function and cellular fitness as untransformed or randomly targeted cells. The frequency of gene replacement with its functional targeting cassette is significantly higher than that of HR-mediated direct gene disruption, and the target gene active variant and marker genes integrated into the genome are flanked by two site-specific recombination sites, which can be easily excised by recombinase.

Secondly, the targeting cassette is excised to leave behind one site-specific recombination site on the target locus and yield target gene disruption, when a recombinase expression vector is introduced into the gene replacement transformants. Although the resulting target gene disruption transformants have lost cellular fitness and slowly appeared in a small number, it can be easily identified and picked from the un-excised transformants, because the excision of selectable marker causes the disruption transformants colony to appear in different phenotype colonies, such as colony color change. Later, the counter selective markers in the recombinase expression vector can be used to remove the vector from disruption mutants via counter selection.

In this two-step gene targeting method, any locus in genome can be disrupted with high frequency. Additionally, the selectable markers can be repeatedly used for gene targeting to different loci in genome. It will not be restricted by the limited choice of selection markers in organisms.

In accordance with another aspect thereof, the present invention have developed "targeting vectors", comprising but not limited to parts of target gene active variants, selection markers, site-specific recombination sites, homologous regions, antibiotic resistance genes and replication origins. These parts can be joined to form a circular vector. The circular vector may contain other parts and linkers between the parts if necessary. The invention is also intended to include other forms of targeting vectors as well, which function equivalent. The targeting vector may also be named as the "targeting plasmid". In general, vectors used in recombinant DNA technology are often in the form of "plasmid". In the present specification, the term "vector" and "plasmid" are used interchangeably.

"Target gene active variant" is a DNA segment which may be naturally occurring, or a fragment, variant, or derivative thereof. It can also be any sort of genetic change, including substitution of one segment for another, insertion and deletion of nucleotide, synthetic polynucleotide, and combinations thereof, which provides a functional activity in a manner similar to the wild type gene. Genes from other species having the same function may also be selected as the target gene active variant. Target gene active variant can be positioned and oriented with different promoters, secretion signal sequences if necessary, and transcription terminators. The positioning and orientation of these segments are within the knowledge of persons of ordinary skill in the art. Thus, the target gene active variant is transcribed and translated to express a protein that retains the activity of the naturally occurring target gene product. The target gene active variant can also be the gene with its own promoter and/or terminator. The target gene active variant may also be the gene without promoter and terminator.

The presence or absence of a marker gene provides a detectable phenotype of an organism. One or more markers may be used in order to select and identify for gene targeting events. Various types of markers useful for the invention include, but not limited to, selection markers and screening markers.

Selection markers are usually genes whose expression can make the organism to have phenotype of resistant or susceptible to a specific set of conditions. Selection markers include genes carrying resistance to an antibiotic such as kanamycin, hygromycin, zeocin, bleomycin, spectinomycin, streptomycin, gentamycin, and the like.

Selectable marker systems composed of an auxotrophic mutant host strain and a wild-type biosynthetic gene which complements the host's defect on an incomplete media such as HIS4, LEU2, URA3, ADE1, LYS2, and TRP1 genes in yeast, and other genes known in the art. For example, *S. cerevisiae* or *P. pastoris* HIS4 gene may be employed for transformation of his4 *P. pastoris* strains.

Screening markers transmits a phenotype that is an observable and distinguishable trait.

Screenable markers include fluorescent proteins such as green fluorescent protein (GFP), reporter enzymes such as β-lactamase (BLA), β-glucuronidase, β-galactosidase (lacZ), alkaline phosphatase (AP), glutathione S-transferase (GST), lucifera, and others known in the art.

The target gene active variant and marker gene are flanked by two site-specific recombination sites, one is located at the upstream-side (on the side of 5' end), and another is located at the downstream-side (on the side of 3' end). The target gene active variant and one or more marker genes between the two site-specific recombination sites may be linked to each other by the same or opposite orientation. In a specific embodiment, the site-specific recombination site is loxP site or FRT site. In a preferred embodiment, the site-specific recombination site is loxP site.

The site-specific recombination sites can be excised by site-specific recombinase. As used herein, "site-specific recombinase" refers to any enzyme capable to functionally catalyzes recombination between its corresponding site-specific recombination sites. The site-specific recombinase may be naturally occurring, or a recombinantly expressed polypeptide, fragment, variant, or derivative that retains the activity of the naturally occurring recombinase. Site-specific recombination systems are reviewed in Craig (1988) Annu. Rev. Genet. 22, 77-105. Any site-specific recombination can be used in the invention. Examples of site-specific recombination systems suitable for this invention include the Cre-loxP from bacteriophage P1, Flp-FRT from *Saccharomyces cerevisiae*, R—RS from *Xygosaccharomyces rouxii* and the like. Each system consists of recombinases that catalyze recombination between recognition sites loxP, FRT, or RS, respectively. In a specific embodiment, the recombinase is Cre recombinase or Flp recombinase. In a preferred embodiment, the recombinase is Cre recombinase.

The site-specific recombination sites are flanked by homologous sequences respectively. The upstream-side one of the homologous sequence is homologous to a region upstream of the target gene, and the downstream-side one of the homologous sequence is homologous to a region downstream of the target gene.

Herein, a region that is "homologous" to the corresponding gene region means a region that has a sequence at least 90%, preferably at least 92%, more preferably at least 94%, still more preferably at least 96%, still more preferably at least 98%, still more preferably at least 99%, and most preferably at 100% identical to the base sequence of the region referred to. Preferably, this "homologous region" is derived from the region referred to.

The length of the homologous recombination regions is not particularly limited. It is preferable that a region has a length suitable for allowing homologous recombination to occur. Therefore, the region may have a length of at least 40 base pairs.

When it is contemplated to pass a vector of the invention though bacterial cells, it is desirable to include a bacterial origin of replication and antibiotic resistance gene in the vector, to ensure the maintenance of the vector from generation to generation of the bacteria. Bacterial origins of replication include the fl-ori, colisin, col El, and others known in the art. Antibiotic resistance genes include ampicillin, kanamycin, tetracycline resistance genes and other known in the art.

In accordance with another aspect, the present invention provides a linear "targeting cassette", which can be linearlized from cyclic targeting vector by restriction enzyme digestion or can be chemically synthesized in the gene of art. This targeting cassette may also be called herein a "targeting fragment", "fragment for gene disruption" or "fragment for gene integration" for convenience. This targeting cassette is used to replace the target gene and integrate exogenous genes into chromosome genome of host such that exogenous genes can perform functions in the host.

The essential parts of targeting cassette include target gene functional variation, selectable marker, site-specific recombination sites, and homologous regions. Target gene active variant can be positioned and oriented with or without different promoters, secretion signal sequences if necessary, and transcription terminators in the targeting cassette. The target gene active variant may not comprise promoter and terminator. The targeting cassette may contain other parts and linkers between the parts if necessary. The target gene active variant and marker gene are flanked on upstream and downstream sides with site-specific recombination sites, respectively. The upstream and downstream sides of site-specific recombination sites are further flanked with homologous regions. The targeting cassette may contain linkers between parts if necessary.

The targeting cassette or vector is introduced into host cells for homologous recombination. Transformation and transfection of host cells may be carried out according to a method well known to those skilled in the art.

Suitable methods of transformation include viral infection, transfection, conjugation, protoplast fusion, electroporation, particle gun technology, calcium phosphate precipitation, direct micro injection, and the like. The choice of method is generally dependent on the type of cell being transformed and the circumstances under which the transformation is taking place. A general discussion of these methods can be found in Ausubel, et al., Short Protocols in Molecular Biology, 3rd ed., Wiley & Sons, 1995.

For example, yeast transformation can be performed with different procedures including, spheroplast procedure, electroporation, polyethylene glycol procedure, alkali cation procedure and the like [Gregg J M (2010) *Pichia* Protocols, Second edition. Totowa, N.J.: Humanna Press].

Examples of the host cell useful in the present invention include typical eukaryotic and prokaryotic hosts, such as *E. coli, Pseudomonas* spp., *Bacillus* spp., *Streptomyces* spp., fungi and yeasts, insect cells, such as *Spodoptera frugiperda* (SF9), animal cells, such as CHO and mouse cells, African green monkey cells, cultured human cells, and plant cells. Yeasts are preferably host cells in the present invention. *P. pastoris* is more preferable host cells.

The transformed cells were then selected based on phenotype of the marker gene. Some marker genes provide a color change phenotype in host cells. In the present invention, it is preferred to use marker gene for colony color change, which facilitates to easily identify and pick gene disruption transformants.

Since the target gene in the genome is replaced by a target gene active variant, the gene transformant maintains biological function and cell suitability similar to the untransformed or randomly targeting host cells. Therefore, any gene in an organism can be efficiently replaced by a target cassette via homologous recombination. In the present invention, these gene substituting hosts are named as "neutral variant strains" or "neutral variant cells". The "neutral variant strain" or "neutral variant cell" means that there is a variation in the strain or cell genome, for example, a change in DNA sequence contained therein, but such alteration does not result in substantial changes in function of the encoded protein, and then does not produce beneficial or harmful effects to the strain or the cell itself.

According to the method of gene targeting of the present invention, a skilled person can engineer a strain; in particular, can engineer a gene in the strain, the disruption efficiency of which is lower than 3% by using conventional targeting methods. Additionally, a method for engineering a strain is provided in the present invention, and the engineered strain can be used in preparation of recombinant proteins. In a specific embodiment, the glycosylation pattern in the recombinant protein is altered. For example, the glycosylation pathway of a protein in a strain can be altered by knocking out OCH1 gene; and degradation of the recombinant protein can be reduced by knocking out the gene of protease in a strain, etc.

The gene targeting method of the present invention can be applied to engineering the biological metabolic reaction of a strain, thereby more efficiently producing metabolites. In a specific embodiment, the metabolite includes (but not limited to), isobutanol, lactic acid, and the like. Moreover, the gene targeting method of the present invention can be applied to alter the enzymatic activity in an organism so that the engineered organism can carry out bio-catalytic reactions more efficiently. For example, the strain engineered by the gene targeting method of the present invention can be used to increase the reaction efficiency of converting glucose to phenylethanol. Therefore, a strain engineered by the method of the present invention can also be used in various fields, such as metabolic engineering, genetic research and biotechnology applications.

In accordance with another aspect thereof, a recombinase expression vector was developed in the present invention, comprising the parts of site-specific recombinase, selection markers, counter selection marker, and replication origin. However, the recombinase expression vector may contain other parts and linkers between the parts if necessary. In the recombinase vector, the site-specific recombinase gene is generally under the control of constitutive promoter. The counter selective marker under the control of constitutive or inducible promoter in the vector allows for selection of cells that lose the recombinase expression vector on their own later. Counter selective markers include mazf, URA3, URA5, and others known in the art. These markers are often toxic or otherwise inhibitory to replication under certain conditions. Selective conditions often involve exposure to a specific substrates or shift in growth conditions.

The recombinase expression vector is introduced into the neutral variant strains by transformation or transfection methods well known to those skilled in the art, so that site-specific recombinase is produced in these strains. The recombinase can efficiently excise the targeting cassette of target gene active variant and marker gene at the site-specific recombination sites, leading to the target gene deletion and leave a single site-specific recombination site at the target locus in genome. Meanwhile, the excision of marker gene results in colony phenotype change, such as colony color change, and facilitates the precise identification of disruption mutants, which have lost cellular fitness and grown slowly in a small number. In the present invention, host cells with the deletion of target gene are named as "target gene disruption mutants", "gene disruption mutants", "disruption mutants", "target gene disruption cells" or "disruption cells". Later, the disruption mutant can lose the recombinase expression vector under certain condition for counter selective marker.

Advantages of the Present Invention

1. Efficiency of gene targeting can be enhanced by the method of the invention;
2. Identification of disruption mutants can be simplified by the method of the invention;
3. Any gene in an organism can be engineered by the method of the invention;
4. Selection marker can be repeatedly used in gene targeting; and
5. A general selection system which is not limited to the selection of markers in an organism is provided in the present invention, for example, the combination of BLA and zeocin$^r$ cassettes will provide a selection system for wild and mutated yeast or other organisms.

EXAMPLE

Materials

The chemicals, enzymes, media and solutions used for the creation, verification and application of the libraries are commonly used and well known for a person skilled in the art of molecular and cell biology; they are available from a number of companies including Thermo Fisher Scientific, Invitrogen, Sigma, New England BioLabs. Takara Biotechnology, Toyobo, TransGen Biotech, and Generay Biotechnology et al. Many of them are provided in kits.

pPICZα vector are from Invitrogen.

pBLHIS-SX, pBLURA-SX, pBLADE-SX vector was obtained from Keck Graduate Institute (KGI).

*E. coli* strain Trans1-T1 was obtained from TransGen Biotech.

*Pichia pastoris* auxotrophic strains JC301 (ade1 his4 ura3) and JC307 (his4 ura3) are obtained from Keck Graduate Institute (KGI), GS115 (his) from Invitrogen.

Nucleotide sequence data were primarily obtained from the public database NCBI (www.ncbi.nlm.nih.gov).

Methods

Unless indicated otherwise, the methods used in this invention including Polymerase Chain Reaction (PCR), restriction enzyme cloning, DNA purification, bacterial and eukaryotic cell cultivation, transformation, transfection, and Western blotting were performed in a standard manner well known for a person skilled in the art of molecular and cell biology, and such as described in the following manuals: Sambrook J et al. (Molecular Cloning A Laboratory Manual (Third Edition), Cold Spring Harbor Laboratory Press, Cold Spring Harbor, N.Y., 2001), Ausubel F M et al. (Current Protocols in Molecular Biology, Wiley InterScience, 2010), and Gregg J M (*Pichia* Protocols, (Second edition), Totowa, N.J.: Humanna Press, 2010).

An *E. coli* strain Trans1-T1 was used for the construction and amplification of plasmids. The strain was grown in Luria-Bertani (LB) medium (10 g/L of tryptone, 5 g/L of yeast extract, and 5 g/L of sodium chloride) or LB plate (15 g/L agar) with appropriate antibiotic. Antibiotics were added at the following concentrations: 100 mg/L of ampicillin, 50 mg/L kanamycin, and 25 mg/L Zeocin).

*P. pastoris* strains were grown in YPD medium (10 g/L yeast extract, 20 g/L peptone, 20 g/L dextrose) and YPD plate (10 g/L yeast extract, 20 g/L peptone, 20 g/L dextrose, 15 g/L agar). *P. pastoris* auxotrophic strains were selected on YNB medium without amino acids (67 g/L yeast nitrogen base, 5 g/L dextrose) and YNB plate without amino acids (67 g/L yeast nitrogen base, 5 g/L dextrose, 15/L agar), supplemented as appropriate. Antibiotics were added at the following concentrations: 500 mg/L G-418 sulphate, and 100 mg/L Zeocin).

Genomic DNA was extracted from yeast by using lithium acetate-SDS lysis followed by ethanol precipitation, which is described in the following publication: Looke et al. 2011, Biotechniques. 50: 325-328.

Transformation of *Pichia pastoris* was performed by electroporation with MicroPulser™ electroporation apparatus following manufacturer (BioRad) operating instructions.

Example 1

Construction of OCH1 Targeting Vector pADE1-OCH1-loxP

FIG. 1 depicts a scheme to construct vector of pADE1-loxP, which could be used to construct gene targeting vectors for *P. pastoris* ade1 auxotrophic strain.

PCR1, KpnIloxADE1 F (The primer has a Kpn I restriction enzyme site, and a lox P site) and ADE1Gp R (The primer has GAP promoter overlapping sequence for fusion PCR) primer pair was used for amplification of ADE1 expression cassette using pBLADE-SX expression vector as a template;

PCR2, AGAPp F (SEQ ID NO: 3; The primer has ADE1 overlapping sequence for fusion PCR) and GAPpMNBX R ((SEQ ID NO: 4; The primer has Mlu I, Not I, BamH I, and Xho I restriction enzyme sites) primer pair were used for PCR amplification of *Pichia pastoris* glyceraldehyde-3-phosphate dehydrogenase (GAP) promoter (GAP P) using genomic GAP gene as a template;

PCR3, the above two PCR products (1, 2) were joined by overlap-extension PCR using KpnIloxADE1 F (SEQ ID NO: 1) and GAPpMNBX R (SEQ ID NO: 4) primer pair. This yielded a fusion fragment of ADE1-PGAP.

PCR4, MNBXTIF51Att F (SEQ ID NO: 5, The primer has Mlu I, Not I, BamH I, and Xho I restriction enzyme sites) and TIF51AttloxNdeI R (SEQ ID NO: 6, The primer has a lox P site and Nde I restriction enzyme site) primer pair were used for PCR amplification of *S. cerevisiae* TIF51A transcription terminator sequence (TIF51A TT) using *S. cerevisiae* genomic DNA as a template;

PCR5, KEAmp F (SEQ ID NO: 7, The primer has Kpn I and EcoR I restriction enzyme sites) and oriSN R (SEQ ID NO: 8, The primer has Sse8387 I and Nde I restriction enzyme sites) primer pair was used to perform PCR amplification of ampicillin resistance gene (Amp$^r$) and replication origin (ori) using pUC19 vector (Generay) as a template.

After PCR product was digested with restriction enzymes, KpnI-BamHI fragment of ADE1-PGAP, BamHI-NdeI fragment of TIF51A TT, and KpnI-NdeI fragment of Amp$^r$-ori were circularized by T4 ligase (Toyobo). This yielded a circular vector pADE1loxP, which was used to construct targeting vector (FIG. 1).

Figure 2:
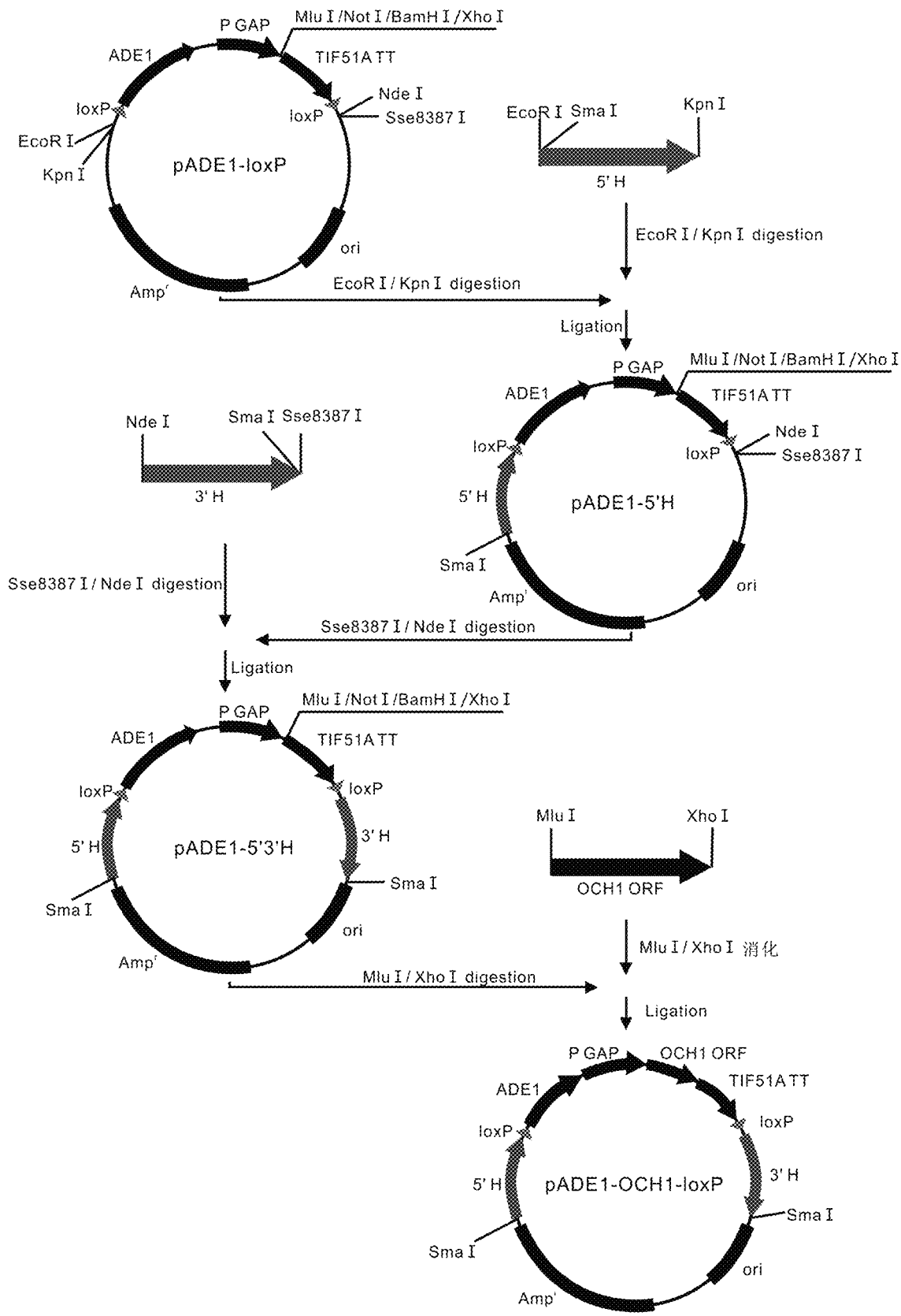
FIG. 2 depicts a scheme to construct pADE1-OCH1-loxP vector, which is used as a targeting vector for OCH1 locus replacement (DNA sequence of OCH1 gene of Pichia pastoris is shown in SEQ ID NO: 58). Vector components are not drawn to scale.

FIG. 2 depicts a scheme to construct a gene targeting vector, pADE1-OCH1-loxP for OCH1 locus disruption in *P. pastoris* add 1 auxotrophic strain.

PCR6, ES5'OCH1 F (SEQ ID NO: 9, The primer has EcoR I and Sma I restriction enzyme sites) and 5'OCH1KpnI R (SEQ ID NO: 10, The primer has Kpn I restriction enzyme site) primer pair was used to PCR amplify the upstream region (on the side of 5' end) of OCH1 ORF using *P. pastoris* genomic DNA as a template. This yielded a 1014 bp fragment, which is used as 5' homologous sequence (5'H) in gene targeting.

Next, the digested EcoRI-KpnI fragment of 5'H was inserted into the same restriction enzyme sites of pADE1loxP vector to yield pADE15'H vector.

PCR7, NdeI3'OCH1 F (SEQ ID NO: 11, The primer has Nde I restriction enzyme site) and 3'OCH1SS R (SEQ ID NO: 12, The primer has Sma I and Sse8387 I restriction enzyme sites) primer pair was used to PCR amplify the downstream (on the side of 3' end) of OCH1 ORF using *P. pastoris* genomic DNA as a template. This yielded a 1008 bp fragment, which is used as 3' homologous sequence (3'H) in gene targeting.

Next, the digested NdeI-Sse83871 fragment of 3'H was inserted into the same restriction enzyme sites of pADE15'H vector to yield pADE15'3'H.

PCR8, MluIOCH1 F (SEQ ID NO: 13, The primer has Mlu I restriction enzyme site) and OCH1XhoI R (SEQ ID NO: 14, The primer has Xho I restriction enzyme site) primer pair was used for PCR amplification of OCH1 ORF from start codon to stop codon using *P. pastoris* genomic DNA as a template.

Next, the digested MluI-XholI fragment of OCH1 ORF was inserted into the same restriction enzyme sites of pADE15'3'H vector to yield a gene targeting vector of pADE1-OCH1-loxP, which could be used for integration by homologous recombination to replace genomic OCH1 ORF in *P. pastoris* ade1 auxotrophic strain (FIG. 2).

Example 2

Construction of mazf and cre Expression Vector, pMaz-Cre

Figure 3:
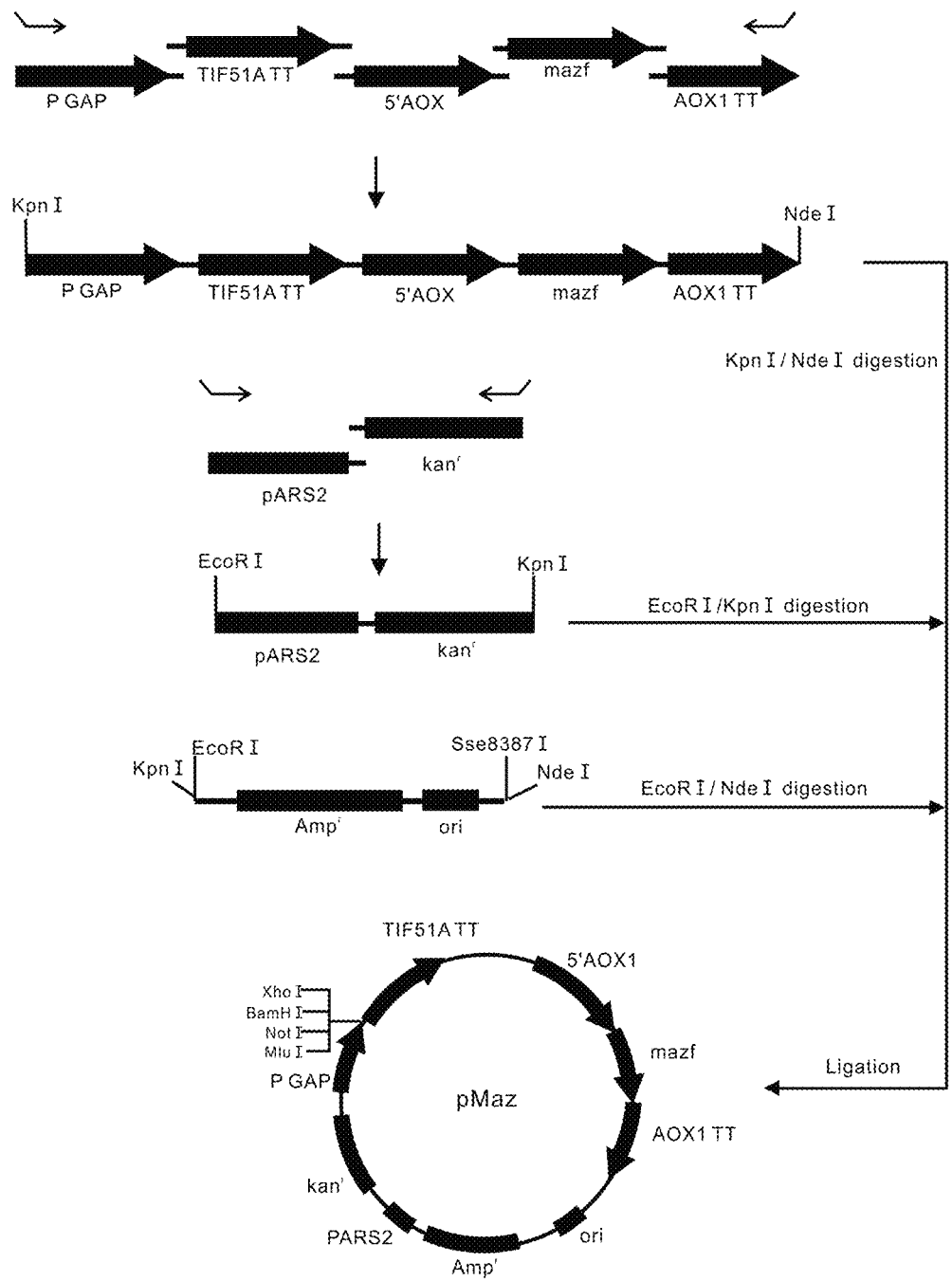
FIG. 3 depicts a scheme to construct pMaz vector. Vector components are not drawn to scale.

FIG. 3 depicts a scheme to construct a mazf expression vector of pMaz.

PCR1, KpnIGAPp F (SEQ ID NO: 15, The primer has Kpn I restriction enzyme site) and GAPpT R (SEQ ID NO: 16, The primer has TIF51A terminator overlapping sequence for fusion PCR) primer pair was used for PCR amplification of *P. pastoris* GAP promoter (P GAP) using genomic DNA as a template.

PCR2, GTIF51Att F (SEQ ID NO: 17, The primer has GAP promoter overlapping sequence for fusion PCR); TIF51AttA R (SEQ ID NO: 18, The primer has 5'AOX1 overlapping sequence for fusion PCR) primer pair was used for PCR amplification of *S. cerevisiae* TIF51A transcription terminator (TIF51A TT) using genomic DNA as a template;

PCR3, TAOX1p F (SEQ ID NO: 19, The primer has TIF51A TT overlapping sequence for fusion PCR) and AOX1pm R (SEQ ID NO: 20, The primer has mazf overlapping sequence for fusion PCR) primer pair was used for PCR amplification of 5' promoter region of *P. pastoris* alcohol oxidase (5'AOX1) using genomic DNA as a template;

PCR4, Amazf F (SEQ ID NO: 21, The primer has 5'AOX1 overlapping sequence for fusion PCR) and mazfAt R (SEQ ID NO: 22, The primer has AOX1 TT overlapping sequence for fusion PCR) primer pair was used to PCR amplify the mazf ORF (SEQ ID NO: 61) from start codon to stop codon using *E. Coli* BL21(DE3) genomic DNA as a template;

PCR5, mAOXt F (SEQ ID NO: 23, The primer has mazf overlapping sequence for fusion PCR); AOXtNdeI R (SEQ ID NO: 24, The primer has Nde I restriction enzyme site) primer pair was used for amplification of *P. pastoris* AOX1 transcription terminator sequence (AOX1 TT) using genomic DNA as a template;

The above five PCR products (1, 2, 3, 4, 5) were joined by overlap-extension PCR using KpnIGAPp F (SEQ ID NO:

15) and AOXtNdeI R (SEQ ID NO: 24) primer pair. It yielded a fragment of PGAP-TIF51ATT-5'AOX1-mazf-AOX1TT (FIG. 3).

PCR6, EcoRIARS2 F (SEQ ID NO: 25, The primer has EcoR I restriction enzyme site) and ARS2k R (SEQ ID NO: 26, The primer has kanamycin resistance cassette overlapping sequence for fusion PCR) primer pair was used for PCR amplification of pARS2, an autonomous replication sequence of *P. pastoris*, using genomic DNA as a template;

PCR7, Akan F (SEQ ID NO: 27, The primer has pARS2 overlapping sequence for fusion PCR) and kanKpnl R (SEQ ID NO: 28, The primer has Kpn I restriction enzyme site) primer pair was used for PCR amplification of kanMX module (kan$^r$) using chemically synthesized kanMX module (SEQ ID NO: 59) as a template. kanMX module is Kanamycin and Geneticin resistance in *E. coli* and *P. pastoris*, respectively;

PCR8, the above two PCR products (6, 7) were joined by overlap-extension PCR using EcoRIARS2 F (SEQ ID NO: 25) and kanKpnl R (SEQ ID NO: 28) primer pair. It yielded a fragment of PARS2-kan$^r$ (FIG. 3).

PCR9, KEAmp F (SEQ ID NO: 7, The primer has Kpn I and EcoR I restriction enzyme sites); and oriSN R (SEQ ID NO: 8, The primer has Sse8387 I and Nde I restriction enzyme sites) primer pair was used to perform PCR amplification of ampicillin resistance gene (Amp$^r$) and replication origin (ori) using pUC19 vector (Generay) as a template. This yielded a fragment of Ampr-ori.

After the product was digested with restriction enzymes, KpnI-NdeI fragment of PGAP-TIF51ATT-5'AOX1-mazf-AOX1TT, EcoRI-KpnI fragment of PARS2-kanr and EcoRI-NdeI fragment of Amp$^r$-ori were circularized using T4 ligase (Toyobo). This yielded mazf expression vector of pMaz, which was used next to construct mazf and cre expression vector (FIG. 3).

Figure 4:
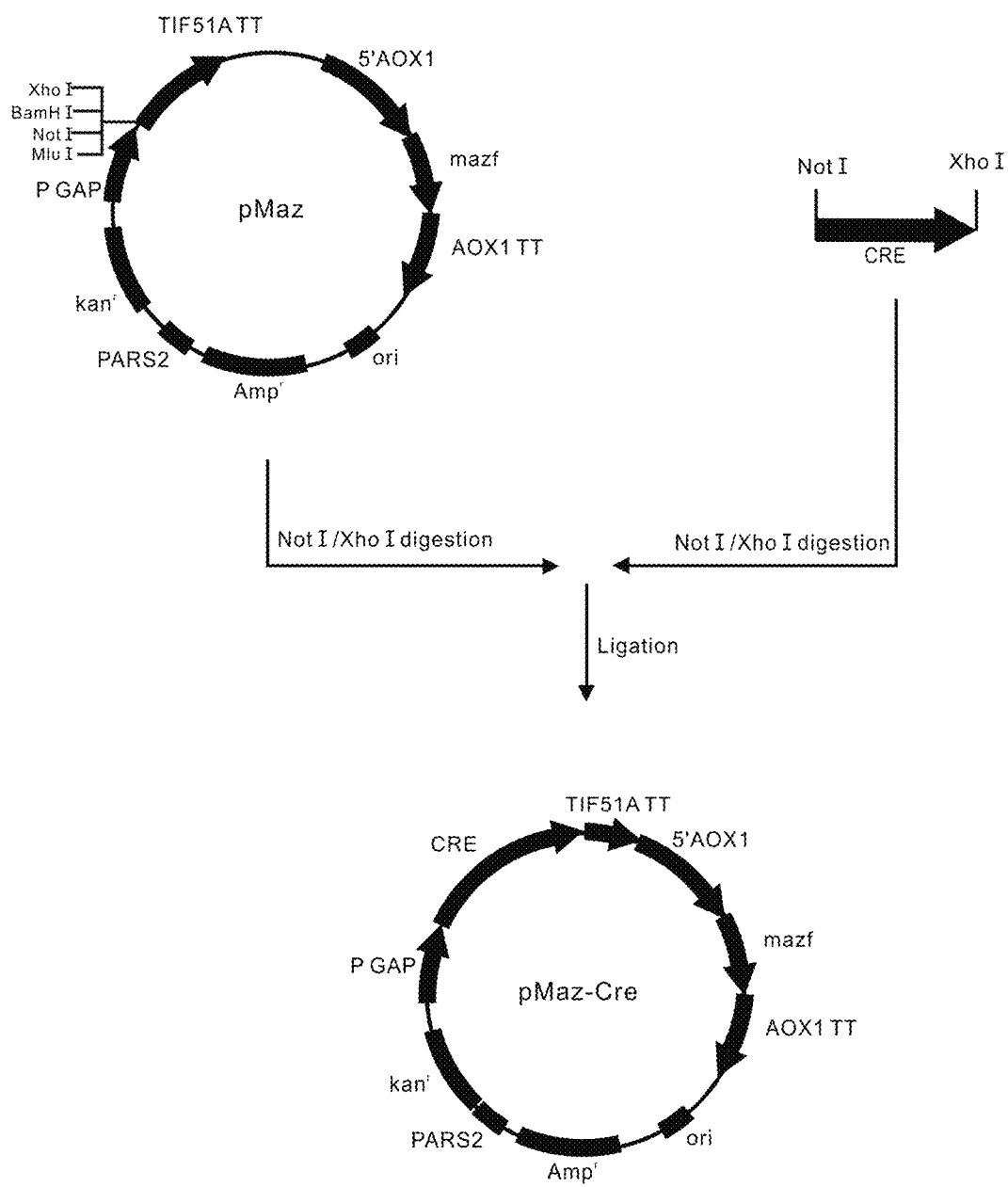
FIG. 4 depicts a scheme to construct pMaz-Cre vector. Vector components are not drawn to scale.

FIG. 4 depicts a scheme to construct mazf and cre expression vector by using pMaz vector.

PCR1, Not1 Cre F (SEQ ID NO: 29, The primer has Not I restriction enzyme site) and CreXhoI R (SEQ ID NO: 30, The primer has Xho I restriction enzyme site) primer pair was used for PCR amplification of cre gene using pSH47 vector (Biovector) as a template. After restriction enzyme digestions, NotI-XhoI fragment of cre gene was inserted into the same restriction enzyme sites of pMaz vector. This yielded the mazf and cre expression vector of pMaz-Cre (FIG. 4). In this vector, high expression of cre is driven by constitutive GAP promoter, but mazf expression is driven by the methanol inducible AOX1 promoter.

Example 3

Figure 5A:
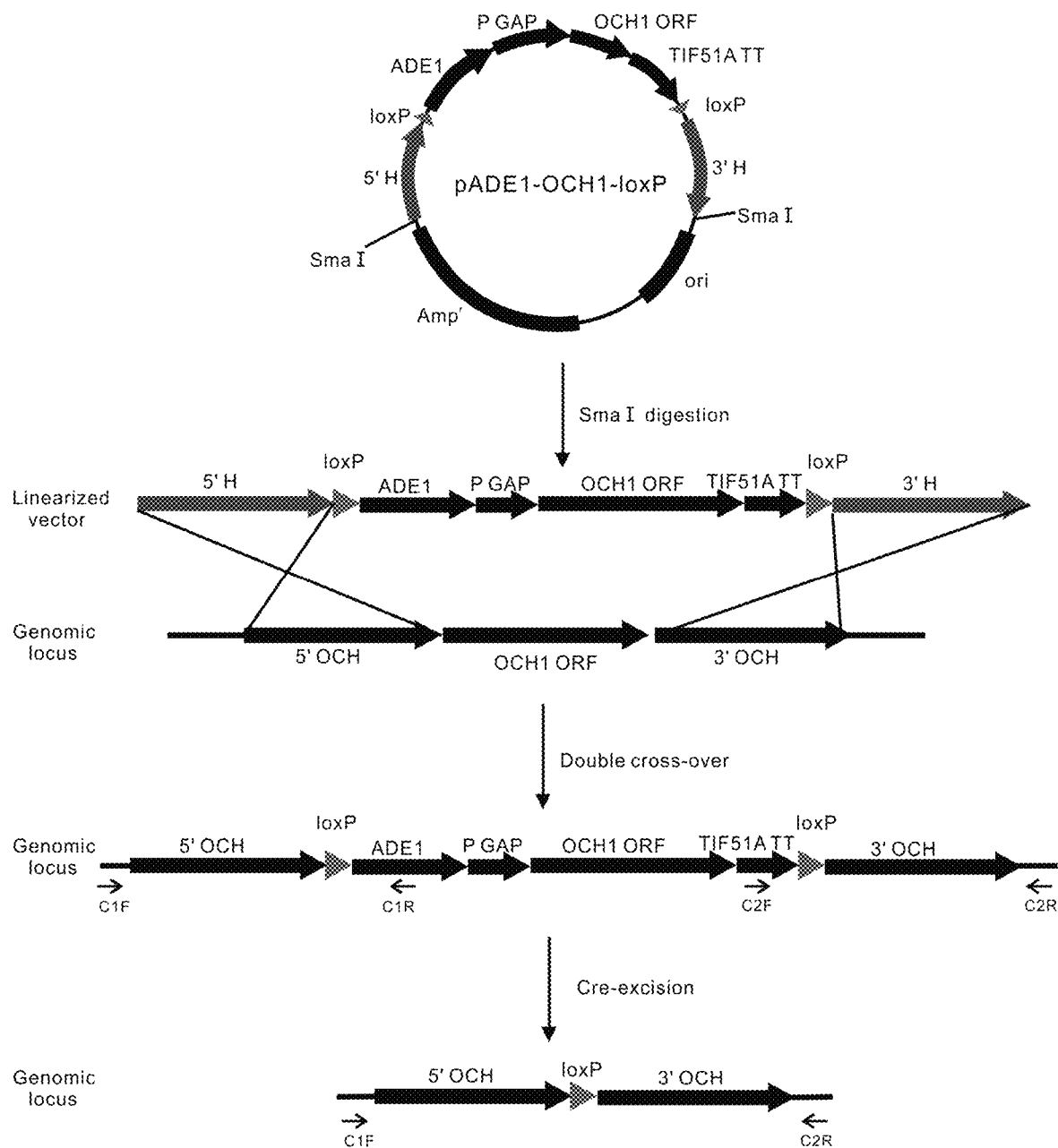
FIG. 5 depicts a scheme and shows results of two-step gene targeting at OCH1 locus in *P. pastoris* genome by targeting vector pADE1-OCH1-loxP. Vector components are not drawn to scale. A: The procedure for genomic OCH1 gene deletion. The targeting vector was linearized with SmaI and integrated to replace OCH1 ORF in *P. pastoris* genome by double cross-over (knock-in) homologous recombination. Next, the cre expression vector (pMaz-Cre) was introduced into the integration strain for site-specific recombination between two loxP sites, which excises ADE1 and OCH1 and leaves behind a single loxP site at OCH1 ORF in genome. B: PCR analysis of integration strains. M, DNA size marker; lane 1 and 2, vector integrations at OCH1 locus give 2018 and 1476 bp bands by PCR with C1 F/C1 R and C2 F/C2 R primer pairs, respectively. C: PCR analysis of post-excision strains. M, DNA size marker; lane 1, Wild-type OCH1 in JC301 strain gives a 3485 bp band by PCR with C1 F/C2 R primer pair; lane 2, och1 deletion in JC301-OCH1::loxP strain gives a 2316 bp band by PCR with C1 F/C2 R primer pair.

Disruption of OCH1 Locus with pADE1-OCH1-loxP vector (1) Replacing OCH1 ORF in Genome Via Homologous Recombination FIG. 5A depicts a scheme of two-step gene targeting at OCH1 locus in *P. pastoris* genome by targeting vector of pADE1-OCH1-loxP.

The targeting vector of pADE1-OCH1-loxP was digested with the restriction enzyme Sma I to generate a linear form of OCH1 targeting cassette 5'H-loxP-ADE1-OCH1-loxP-3'H. It contains ADE1 expression cassette, which is used as a selectable marker. It also has OCH1 expression cassette, in which OCH1 expression is initiated by GAP promoter and terminated by TIF51A terminator. ADE1 and OCH1 expression cassettes are adjacent in the same strand and orientation, and surrounded on both sides by Cre recombinase target sequences of loxP (ATAACTTCGTATAATGTATGCTATACGAAGTTAT, SEQ ID NO: 31) which are placed in direct orientation to form a fragment of loxP ADE1-OCH1-loxP. The out most parts of the targeting cassette, namely the 5' and 3' integration sequences (5'H and 3'H), are locus-specific homologous sequences, which guarantee to replace the genomic OCH1 ORF by double cross-over homologous recombination. The two homologous 5' and 3' sequences were 1014 and 1008 bp, respectively.

The targeting cassettes were transformed into the cells of *P. pastoris* auxotrophic strains JC301 (ade1 his4 ura3) by electroporation with MicroPulser™ electroporation apparatus following manufacturer (BioRad, USA) operating instructions. The transformed cells were grown on YNB plates supplemented with 20 mg/L histidine and 50 mg/L uracil to select for adenine prototrophy.

Figure 5B:
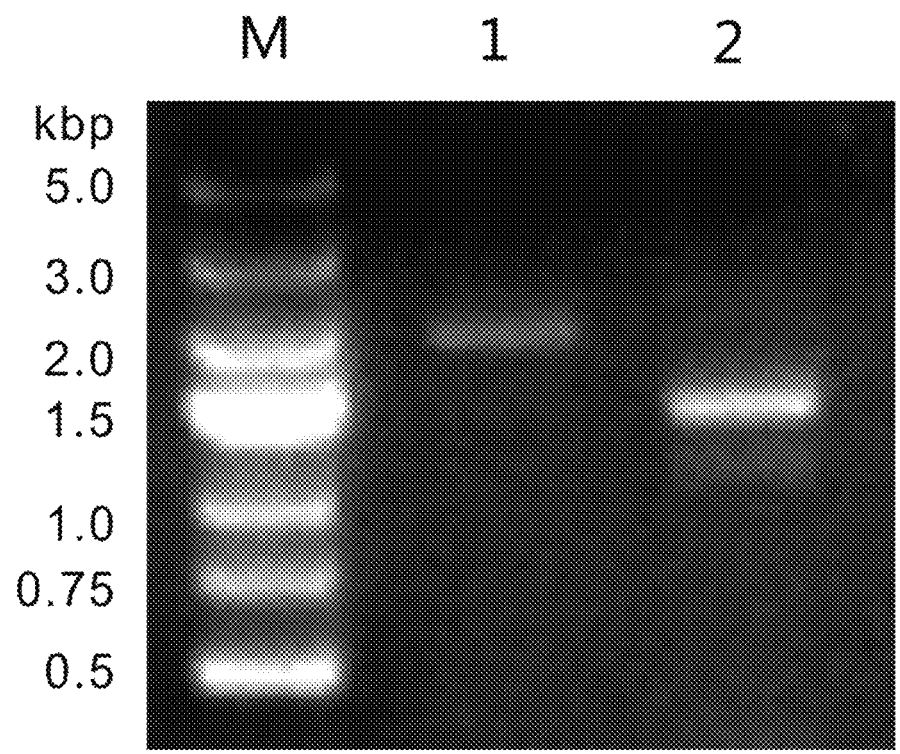

ADE1 expression cassette in the targeting cassette was used as a selectable marker. JC301 (ade1 his4 ura3) appears in pink colony, because this add 1 auxotrophic strain led to the accumulation of a red pigment in cells. Genome integration of targeting cassette by HR and NHEJ pathways yielded ADE1 prototrophy strain, which appeared as white colony. Two primer pairs, C1 F (SEQ ID NO: 32, located upstream of the 5' homologous region in the genome)/C1 R (SEQ ID NO: 33, located within ADE1 cassette) and C2 F (SEQ ID NO: 34, located within TIF51A TT)/C2 R (SEQ ID NO: 35, located downstream of the 3' homologous region in the genome), were used in PCR to verify OCH1 ORF replacement in white colony (FIG. 5A). The successful PCR amplification of both 2018 and 1467 bp bands indicated that the target cassette was successful to homologously integrate on genomic DNA to replace the OCH1 ORF (FIG. 5B). In transformation plate, 20 white colonies were randomly picked and cultured overnight to extract genomic DNA for PCR verification. There were 3 correct integration colonies among these 20 tested white colonies. This OCH1 ORF HR replacement by target gene active variant was very efficient at the frequency of 15% (3/20), when 1014 and 1008 bp of 5' and 3' homologous sequences are used.

The homologous recombination of targeting cassette yielded a OCH1 neutral variant strain JC301-AOP (OCH1::loxP-ADE1-OCH1-loxP), in which OCH1 ORF in genome is replaced with the targeting cassette. The integrated ADE1 and OCH1 expression cassettes are surrounded by two loxP sites of Cre recombinase target sequence.

(2) Excision of Integrated Targeting Cassette by Cre Recombinase.

Figure 5C:
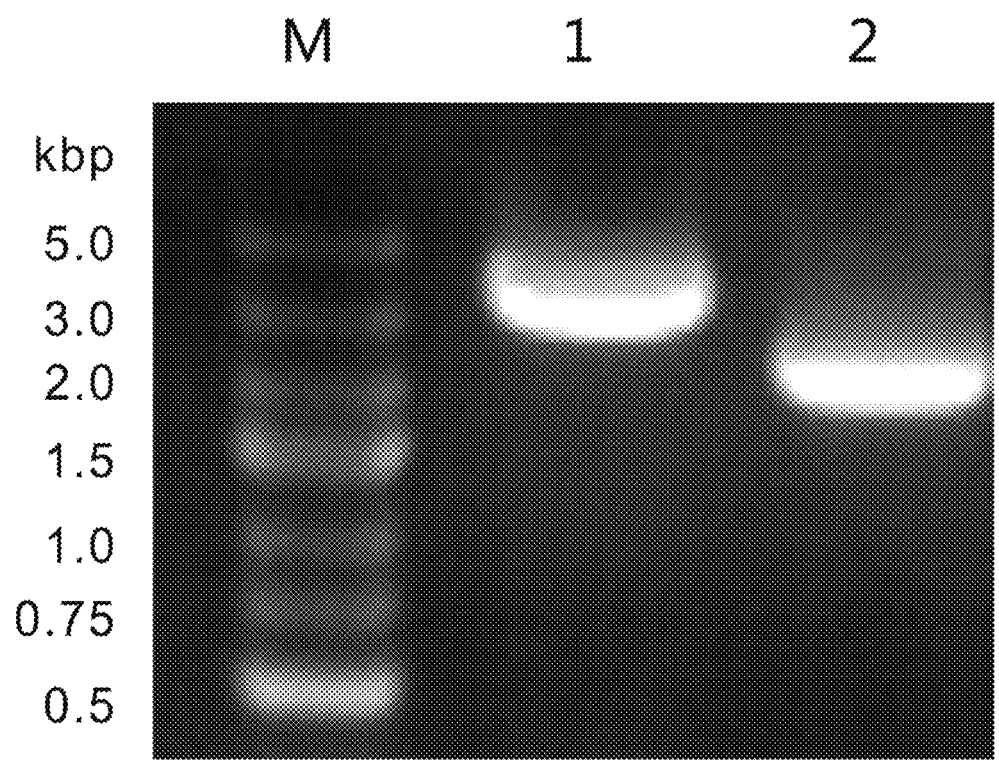

The mazf and cre expression vector of pMaz-Cre carries the cre gene under the control of strong constitutive GAP promoter, and mazf gene under the control of methanol inducible AOX1 promoter. The vector also carries kanamycin resistance gene (kan$^r$) for selection. The OCH1 neutral variant strain JC301-AOP (OCH1::loxP-ADE1-OCH1-loxP) were transformed with pMaz-Cre vector by electroporation and grown on YPD plate supplemented with 200 mg/L Geneticin (G-418 sulphate). Upon expression of the Cre recombinase, the integrated cassette of ADE1 and OCH1 were excised by the site-specific recombination between two loxP sites, leaving behind a single loxP site at OCH1 ORF region in the genome (OCH1::loxP). This yielded och1 deletion and add 1 auxotrophic strain (JC301-OCH1::loxP), which appeared in pink colony. A primer pair of C1 F (SEQ ID NO: 32)/C2 R (SEQ ID NO: 35) was used in PCR to verify the excision of ADE1 and OCH1 cassette (FIG. 5A). The successful PCR amplification of 2316 bp band indicated that the ADE1 and OCH1 cassette was excised to leave a loxP site at OCH1 ORF region in the genome. PCR amplification of 3485 bp band in JC301 strain was used as a control (FIG. 5C).

In YPD plate with Geneticin, most were fast growing large white colonies of neutral variant strain JC301-AOP, but there were a small number of slow growing pink colonies which can be easily observed to pick. 25 pink colonies were randomly picked and cultured overnight to extract genomic DNA for PCR verification. All of these 25 pink colonies were confirmed to be och1 deletion strain (JC301-OCH1::loxP). Therefore, ADE1 selection marker facilitated the selection efficiency for och1 deletion strain at the frequency of 100% in the excision step.

The Cre-mediated excision of targeting cassette has two advantages in this two-step gene targeting method. Firstly, the ADE1 marker provides an efficient selection method to distinguish pink och1 deletion strain from white OCH1 neutral variant strains in the culture plate. Secondly, the excision rescues the ADE1 marker, which can be repeated to use in gene targeting.

Later, the pMaz-Cre vector in och1 deletion strain could be removed by streaking strains on a MM plate (13.4 g/L YNB, 5 ml/L methanol, 20 mg/L histidine, 50 mg/L uracil, 50 mg/L adenine and 0.4 mg/L biotin). Since pMaz-Cre vector has mazf gene under the control of the AOX promoter, methanol in MM plate induces the expression of MazF toxin, which functions as an mRNA interferanse to inhibit the growth of prokaryotes and eukaryotes (Yang et al (2009) Fems Yeast Research 9: 600-609). Therefore, methanol induced MazF production causes a strong selection pressure on och1 deletion strain and forces them to lose pMaz-Cre vector.

In summary, the two-step gene targeting of the invention can efficiently generate och1 deletion strains at the frequency of 15% (15%×100%), when 1014 and 1008 bp of 5' and 3' homologous sequences are used. It overcomes the problem of low efficiency in OCH1 disruption by gene targeting. In previous reports, the disruption of OCH1 locus in *P. pastoris* is low efficient at a frequency of 0.1%, when ~1 kb or more regions of homology are used. But other laboratories reported that OCH1 disruption is hardly to be repeated at this low efficiency (Choi, 2003, Proc Natl Acad Sci USA 100: 5022-5027; Chen, 2013, PLoS ONE 8(3): e57952).

Example 4

Construction of ARG4 Targeting Vector of pBLA-ARG4-loxP

Figure 6:
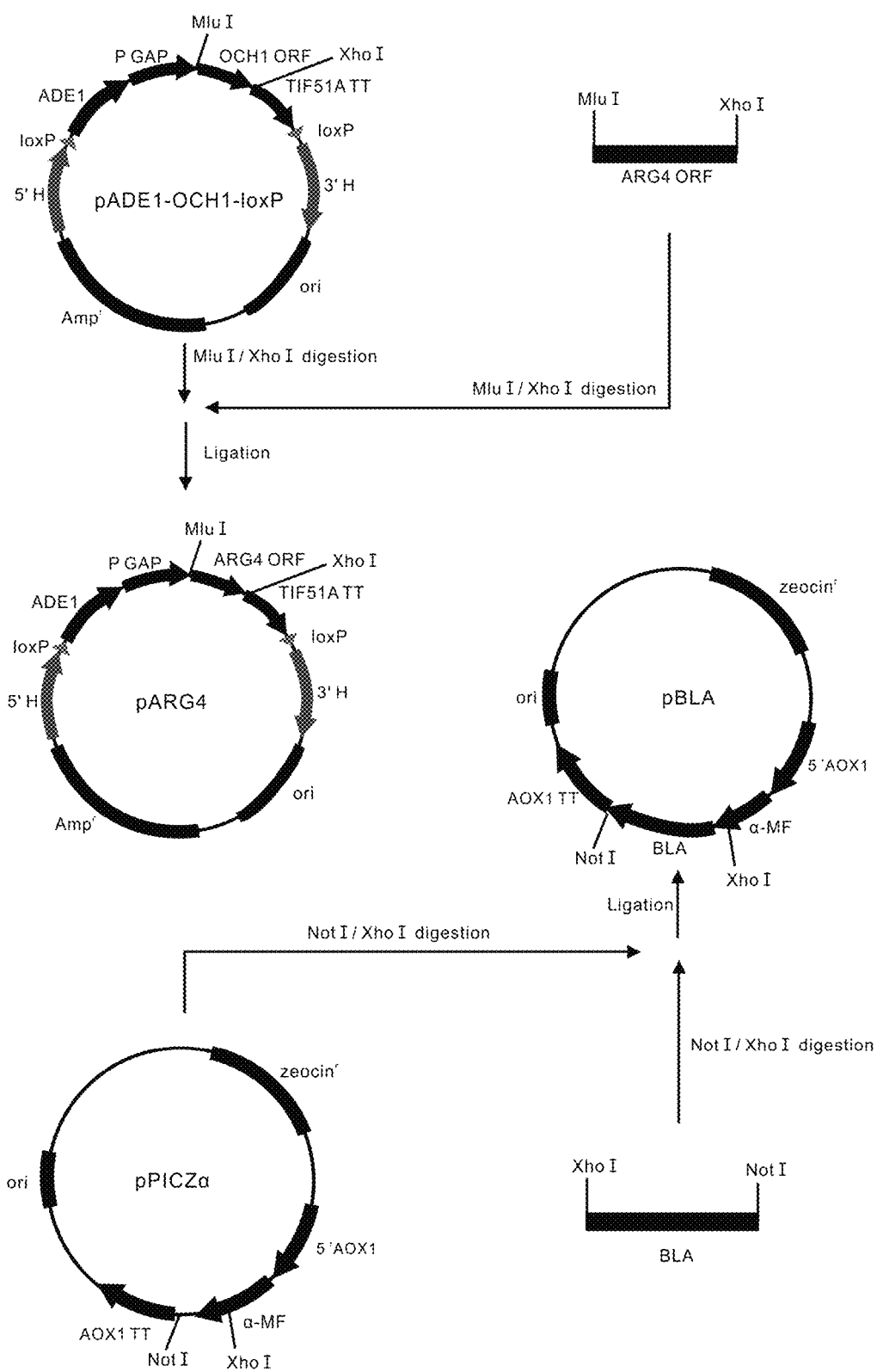
FIG. 6 depicts a scheme to construct pARG4 and pBLA vectors. Vector components are not drawn to scale.

FIG. 6 depicts a scheme to construct pARG4 and pBLA vectors.

PCR1, MluIARG4 F (SEQ ID NO: 36, The primer has a Mlu I restriction enzyme site) and ARG4XhoI R (SEQ ID NO: 37, The primer has a Xho I restriction enzyme site) primer pair were used to PCR amplification of ARG4 ORF using *P. pastoris* genomic DNA as a template;

Next, the digested MluI-XhoI fragment of ARG4 ORF was inserted into the same restriction enzyme sites of pADE1-OCH1-loxP vector to yield a pARG4 vector (FIG. 6).

PCR2, XhoIBLA F (SEQ ID NO: 38, The primer has a Xho I restriction enzyme site) and BLANotI R (SEQ ID NO: 39, The primer has a Not I restriction enzyme site) primer pair were used for PCR amplification of β-lactamase (BLA) ORF without its N-terminal 23 amino acid by using pUC19 vector as a template;

Next, the digested XhoI-NotI fragment of BLA ORF was inserted into the same restriction enzyme sites of pPICZα vector (Invitrogen) to yield a pBLA vector (FIG. 6).

Figure 7:
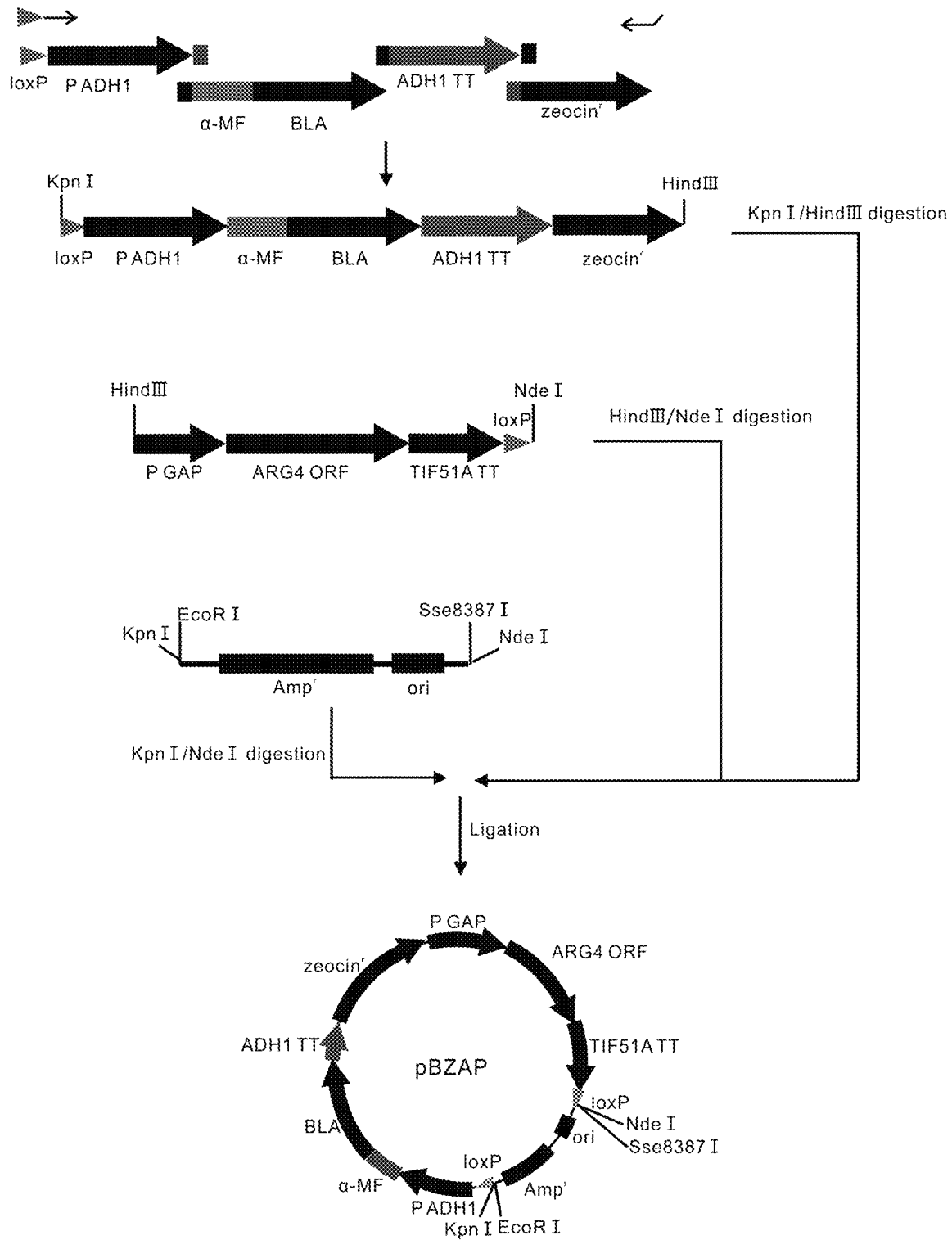
FIG. 7 depicts a scheme to construct pBZAP vector. Vector components are not drawn to scale.

FIG. 7 depicts a scheme to construct pBZAP vector.

PCR1, KpnIloxADH1p F (SEQ ID NO: 40, The primer has a Kpn I restriction enzyme site, and a loxP site) and ADH1pM R (SEQ ID NO: 41, The primer has α-MF overlapping sequence for fusion PCR) primer pair were used for PCR amplification of *S. cerevisiae* ADH1 promoter (P ADH1) using genomic DNA as a template.

PCR2, ApMF F (SEQ ID NO: 42, The primer has ADH1 promoter overlapping sequence for fusion PCR) and BLAAtt R (SEQ ID NO: 43, The primer has ADH1 terminator overlapping sequence for fusion PCR) were used for PCR amplification of MF-BLA fragment using pBLA vector as a template. The MF-BLA fragment contains mating factor signal sequence (α-MF), and BLA ORF.

PCR3, BADH1tt F (SEQ ID NO: 44, The primer has BLA overlapping sequence for fusion PCR) and ADH1ttZ R (SEQ ID NO: 45, The primer has Zeocin$^r$ cassette overlapping sequence for fusion PCR) primer pair was used for PCR amplification of *S. cerevisiae* ADH1 transcription terminator (ADH1 TT) using genomic DNA as a template.

PCR4, AttZeo F (SEQ ID NO: 46, The primer has ADH1 terminator overlapping sequence for fusion PCR) and ZeoHindIII R (SEQ ID NO: 47, The primer has a Hind III restriction enzyme site) primer pair was used for PCR amplification of Zeocin$^r$ cassette (Shble expression cassette) using pBLA vector as a template.

PCR5, the above four PCR products (1, 2, 3, 4) were joined by overlap-extension PCR using KpnIloxADH1p F (SEQ ID NO: 40) and ZeoRHindIII R (SEQ ID NO: 47) primer pair. It yielded a fragment of BLA/Zeocin$^r$ cassette.

PCR6, HindIIIGAPp F (SEQ ID NO: 48, The primer has a Hind III restriction enzyme site) and TIF5lAttloxNdeI R (SEQ ID NO: 49, The primer has a loxP site and Nde I restriction enzyme site) primer pair was used for PCR amplification of ARG4 expression cassette using pARG4 vector as a template.

PCR7, KEAmp F (SEQ ID NO: 7, The primer has Kpn I and EcoR I restriction enzyme sites); and oriSN R (SEQ ID NO: 8, The primer has Sse8387 I and Nde I restriction enzyme sites) primer pair was used to perform PCR amplification of ampicillin resistance gene (Amp$^r$) and replication origin (ori) using pUC19 vector as a template. This yielded a fragment of Amp$^r$-ori.

After PCR product was digested with restriction enzymes, KpnI-HindIII fragment of BLA/Zeocin$^r$ cassette, HindIII-NdeI fragment of ARG4 cassette, and KpnI-NdeI fragment of Amp$^r$-ori were circularized by using T4 ligase. This yielded a circular vector of pBZAP (FIG. 7).

Figure 8:
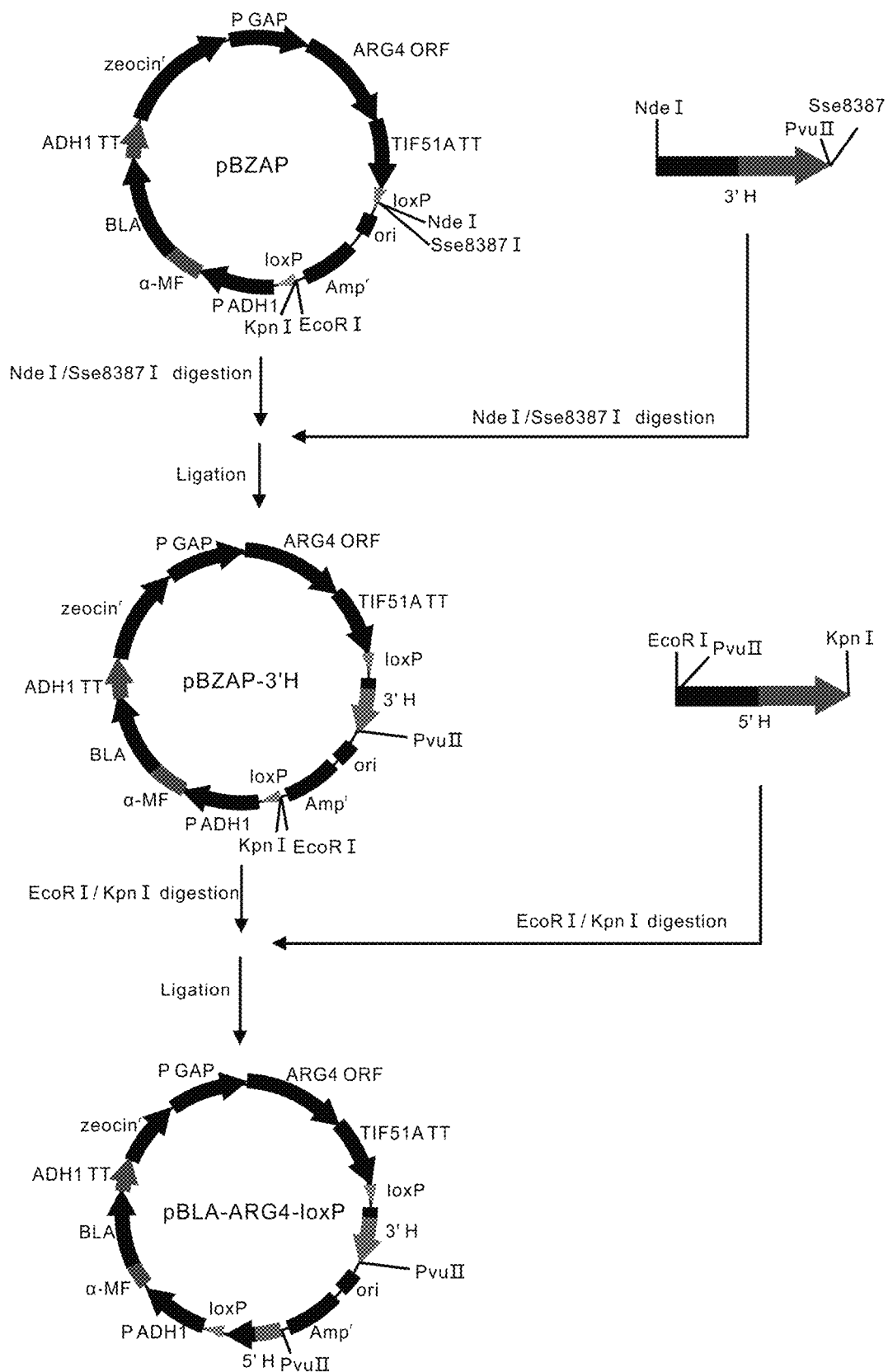
FIG. 8 depicts a scheme to construct pBLA-ARG4-loxP vector, which is used as a targeting vector for ARG4 locus disruption. Vector components are not drawn to scale.

FIG. 8 depicts a scheme to construct pBLA-ARG4-loxP vector, which is used as a targeting vector for ARG4 locus disruption.

PCR1, NdeI3'ARG4 F (SEQ ID NO: 50, The primer has Nde I restriction enzyme site) and 3'ARG4PS R (SEQ ID NO: 51, The primer has Pvu II and Sse8387 I restriction enzyme sites) primer pair was used to PCR amplify the downstream of nucleotide 922 in ARG4 ORF using *P. pastoris* genomic DNA as a template. This yielded a 841 bp fragment (922/+367 bp), which is used as 3' homologous sequence (3'H) in gene targeting. The numbering of the nucleotide for the 5'- and 3'-regions refers to the respective start codon of the coding region as nucleotides 1-3 and the respective stop codon as nucleotides+1 to +3.

Next, the digested NdeI-Sse83871 fragment of 3'H was inserted into the same restriction enzyme sites of pBZAP vector to yield pBZAP3'H.

PCR2, EP5'ARG4 F (SEQ ID NO: 52, The primer has EcoR I and Pvu II restriction enzyme sites) and 5'ARG4KpnI R (SEQ ID NO: 53, The primer has Kpn I restriction enzyme site) primer pair was used to PCR amplify the upstream of nucleotide 515 in ARG4 ORF using *P. pastoris* genomic DNA as a template. This yielded a 797 bp fragment (−282/515 bp), which is used as 5' homologous sequence (5'H) in gene targeting.

Next, the digested EcoRI-KpnI fragment of ARG4 5'H was inserted into the same restriction enzyme sites of pBZAP3'H vector to yield ARG4 targeting vector pBLA-ARG4-loxP, which was used for ARG4 ORF partial knockout (516/921, 406 bp).

Example 5

Disruption of ARG4 Locus with pBLA-ARG4-loxP Vector

Figure 9A:
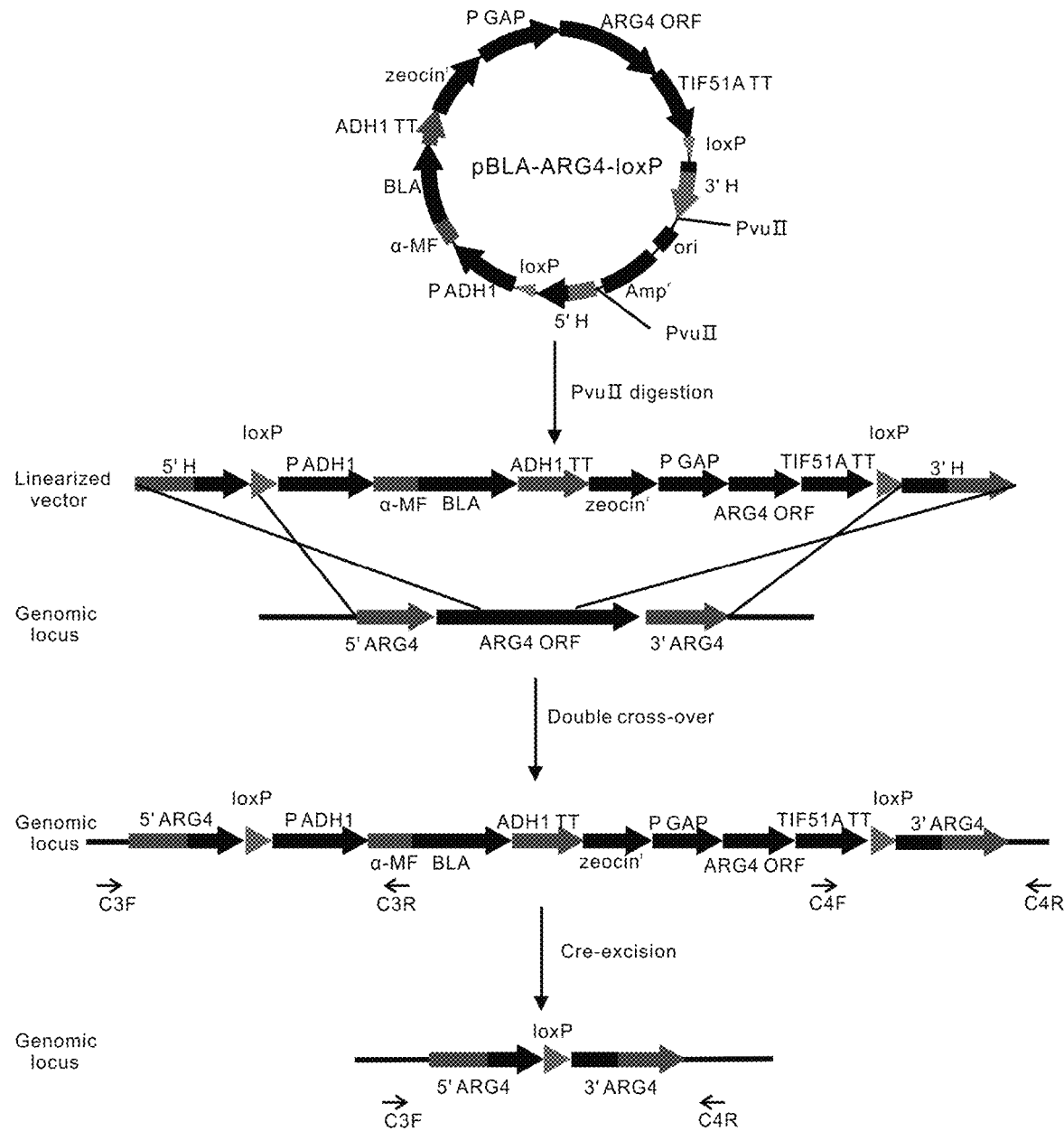
FIG. 9 depicts a scheme and shows results of two-step gene targeting at ARG4 locus in *P. pastoris* genome by targeting vector pBLA-ARG4-loxP. Vector components are not drawn to scale. A: The procedure for partial deletion in genomic ARG4 ORF. The targeting vector was linearized with Pvu II and integrated to replace partial ARG4 ORF (516 to 921 bp) in *P. pastoris* genome by double cross-over (knock-in) homologous recombination. Next, the cre expression vector (pMaz-Cre) was introduced into the integration strain for site-specific recombination between two loxP sites, which excises BLA, zeocinr, and ARG4 to leave behind a single loxP site at ARG4 ORF region between 516 to 921 nucleotides. B: PCR analysis of integration strains. M, DNA size marker; lane 1 and 2, vector integration at ARG4 locus gives 1779 and 1221 bp bands by PCR with C3 F/C3 R and C4 F/C4 R primer pairs, respectively. C: PCR analysis of post-excision strains. M, DNA size marker; lane 1, wild-type ARG4 in GS115 strain gives a 2200 bp band by PCR with C3 F/C4 R primer pair; lane 2, Partial deletion of ARG4 ORF between 516 to 921 nucleotides in GS115-arg4::loxP strain gives a 1840 bp band by PCR with C3 F/C4 R primer pair.

FIG. 9 depicts a scheme of two-step gene targeting at ARG4 locus in *P. pastoris* genome by targeting vector pBLA-ARG4-loxP.

pBLA-ARG4-loxP vector was digested with restriction enzyme Pvu II to generate a linear form of ARG4 targeting cassette 5'H-loxP-BLA-Zeocin-ARG4-loxP-3'H. The targeting cassette has BLA expression cassette as a screening marker and zeocin$^r$ cassette as selection marker. It also has ARG4 expression cassette, which is initiated by GAP promoter and terminated by TIF51A terminator. The BLA, zeocin$^r$, and ARG4 cassettes are adjacent in the same strand, and surrounded on both sides by loxP sites in direct orientation. The out most parts of the targeting cassette are target locus-specific homologous sequences (5'H and 3'H) for the replacement of genomic ARG4 ORF region between nucleotide 515 to 922 by double cross-over homologous recombination. The two homologous 5' and 3' homologous sequences were 797 and 841 bp, respectively (FIG. 9A).

Figure 9B:
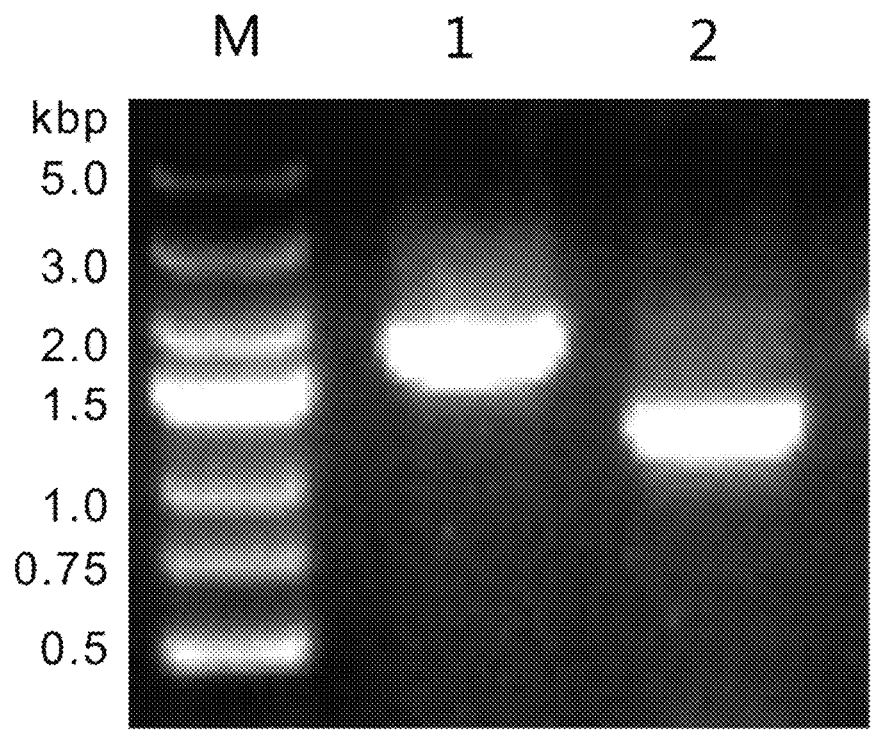

The targeting cassettes were transformed into the cells of *P. pastoris* auxotrophic strains GS115 (his4) by electroporation. The transformed cells were grown on YPD plates supplemented with 100 mg/L zeocin. Genome integration of the targeting cassette by HR and NHEJ pathways yielded zeocin resistant strains. Two primer pairs, C3 F (SEQ ID NO: 54, located upstream of the 5' homologous region in the genome)/C3 R (SEQ ID NO: 55, located within α-MF) and C4 F (SEQ ID NO: 56, located within TIF51A TT)/C4 R (SEQ ID NO: 57, located downstream of the 3' homologous region in the genome), were used in PCR to verify replacement of genome ARG4 ORF between nucleotides 516 to 921 (FIG. 9A). The successful PCR amplification of both 1779 and 1221 bp bands indicated that the target cassette was successful to homologously integrate on genome to replace the ARG4 ORF region between nucleotide 516 to 921 (FIG. 9B). In transformation plate, 9 colonies were randomly picked and cultured overnight to extract genomic DNA for PCR verification. There were 2 correct integration colonies among these 9 tested colonies. This ARG4 ORF replacement by its active variant was very efficient at the frequency of 22% (2/9), when 797 and 841 bp of 5' and 3' homologous sequences are used. This yielded a ARG4 neutral variant strain GS115-ABP (ARG4::loxP-BLA-Zeocin-ARG4-loxP), in which the genome ARG4 ORF region between nucleotide 516 to 921 (406 bp) was replaced with the targeting cassette. The integrated targeting cassette was surrounded by two loxP sites of target sequence of Cre recombinase.

Figure 9C:
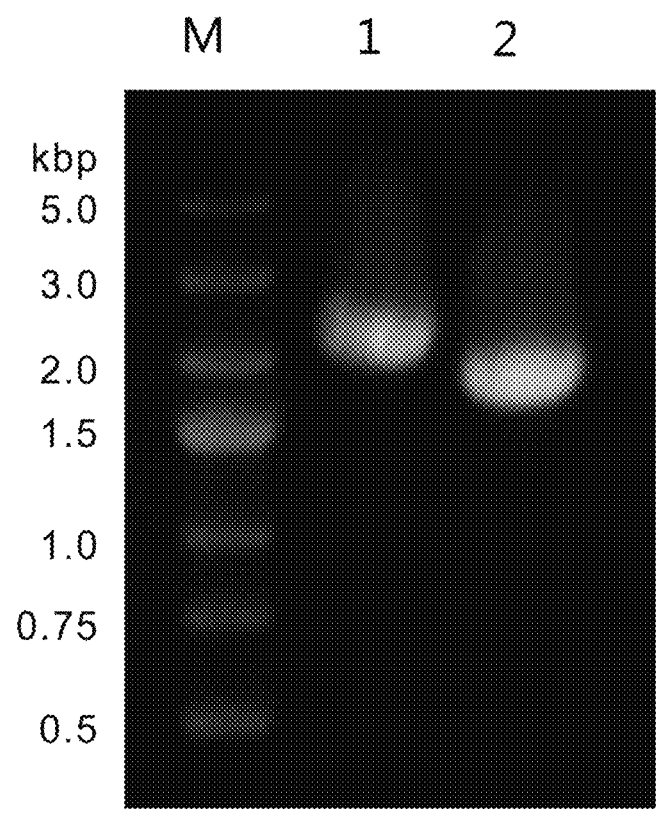

Next, the ARG4 neutral variant strain GS115-ABP were transformed with pMaz-Cre vector by electroporation and grown on YPD plate supplemented with 200 mg/L Geneticin (G-418 sulphate) and 100 mg/L nitrocefin. Colonies of ARG4 neutral variant strain GS115-ABP were brown colored on nitrocefin plate, because the integrated targeting cassette expressed β-lactamase which hydrolyzed nitrocefin colorimetric substrate to yield a colored product. Upon expression of Cre recombinase, the BLA, zeocin$^r$, and ARG4 expression cassettes were excised by the site-specific recombination between two loxP sites, leaving behind a single loxP site at the genomic ARG4 ORF region between nucleotide 516 to 921 in genome (406 bp deletion) (ARG4::loxP). This yielded arg4 partial deletion strains (GS115-arg4::loxP), which appeared in white colonies. A primer pair of C3 F (SEQ ID NO: 54)/C4 R (SEQ ID NO: 57) was used in PCR to verify the excision of integrated cassette (FIG. 9A). The successful PCR amplification of 1840 bp band indicated that the integrated cassette was excised to leave a loxP site at ARG4 ORF region between nucleotide 516 to 921 in the genome. PCR amplification of 2200 bp band in GS115 strain was used as a control (FIG. 9C).

In YPD plate with Geneticin and nitrocefin, many white colonis can be easily identified from brown colonies. 5 white colonies were randomly picked and cultured overnight to extract genomic DNA for PCR verification of Cre-mediated excision. All of these 5 white colonies were confirmed to be arg4 partial deletion strains (GS115-arg4::loxP). Therefore, BLA screening marker facilitated the selection efficiency for arg4 deletion strain at the frequency of 100% in the excision step.

Later, pMaz-Cre vector was removed from the arg4 deletion strain (GS115-arg□loxP) by streaking on MM plate via mazF counter-select.

In this example, deletion of ARG4 ORF in genome by the two-step gene targeting method was efficient at frequency of 22% (22%×100%), when 797 and 841 bp of 5'H and 3'H were used. It is more efficient than the previous reported ARG4 targeting disruption at a frequency of 3%, which uses 963 bp 5'H and 1502 bp of 3'H (Naatsaari L, Mistlberger B, Ruth C, Hajek T, Hartner F S, et al. (2012) Deletion of the *Pichia pastoris* KU70 Homologue Facilitates Platform Strain Generation for Gene Expression and Synthetic Biology. PLoS ONE 7(6): e39720.).

The combination of BLA and zeocin$^r$ cassettes provides a versatile selection system for yeast and other organisms that lack auxotrophic mutants. The excision rescues the BLA and zeocin$^r$ cassettes, which can be repeatedly used in gene targeting. Excision of the BLA marker also provides a simple and efficient method to identify disruption mutants from the integrated neutral variant strains.

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

The invention claimed is:

1. A plasmid construct for altering a genome by gene targeting, comprising the following structure:

5'-A$_1$-B$_1$-C$_1$-C$_2$-X-B$_2$-A$_2$-3';

5'-A$_1$-B$_1$-X-C$_1$-C$_2$-B$_2$-A$_2$-3';

5'-A$_1$-B$_1$-C$_1$-X-B$_2$-C$_2$-A$_2$-3'; or

5'-A$_1$-B$_1$-X-C$_1$-B$_2$-C$_2$-A$_2$-3' wherein

B$_1$ and B$_2$ are site-specific recombination sites;
C$_1$ and C$_2$ are marker genes and cannot be absent at the same time;
X is an active variant of a target gene in the genome;
the active variant possesses a functional activity of the target gene;
A1 is a sequence that is homologous to a region upstream of the target gene in the genome; and
A2 is a sequence that is homologous to a region downstream of the target gene in the genome.

2. The plasmid construct of claim 1, wherein the site-specific recombination sites are loxP site or FRT site.

3. The plasmid construct of claim 2, wherein the site-specific recombination sites are loxP site.

4. The plasmid construct of claim 1, wherein the active variant comprises a promoter and/or terminator.

5. A composition for gene targeting, wherein the composition comprises the plasmid construct of claim 1 and an expression vector for expressing a recombinase.

6. The composition of claim 5, wherein the recombinase is Cre recombinase or Flp recombinase.

7. The composition of claim 6, wherein the recombinase is Cre recombinase.

8. The plasmid construct of claim 1, wherein C$_1$ and C$_2$ are both present.

9. A host cell comprising the plasmid construct of claim 1.

10. The host cell of claim 9, wherein the host cell is a yeast.

11. A method for gene targeting, comprising:
a) constructing the plasmid construct of claim 1;
b) introducing the plasmid construct obtained in step a) into a cell, thereby replacing the target gene in the genome of the cell with the plasmid construct via homogeneous recombination;
c) excising the plasmid construct by a recombinase, thereby leaving behind a site-specific recombination site on the target gene and yielding a mutant of the target gene.

12. The method of claim 11, wherein the recombinase is expressed by an expression vector, and the method further comprises removing the expression vector via a counter-selection marker gene of the expression vector.

13. A method for engineering a strain, comprising:
a) constructing the plasmid construct of claim 1;
b) introducing the plasmid construct obtained in step a) into a strain to be engineered, thereby replacing the target gene in the genome of the strain to be engineered with the plasmid construct via homogeneous recombination;
c) introducing an expression vector for expressing a recombinase in the strain to be engineered, and excising the plasmid construct by the recombinase, thereby leaving behind a site-specific recombination site on the target gene and yielding a disruption mutant of the target gene.

14. The method of claim 13, wherein the method further comprises removing the expression vector via a counter-selection marker gene of the expression vector.

15. A method for producing a recombinant protein, comprising a step of growing a strain engineered according to the method of claim 13 to produce the recombinant protein.

16. A method for producing a metabolite, comprising a step of growing a strain engineered according to the method of claim 13 to obtain the metabolite.

17. A method for performing a biocatalytic reaction, comprising a step of using a strain engineered according to the method of claim 13 in a biocatalytic reaction.

* * * * *

SEQUENCE LISTING

<160> NUMBER OF SEQ ID NOS: 61

<210> SEQ ID NO 1
<211> LENGTH: 68
<212> TYPE: DNA
<213> ORGANISM: Artificial Sequence
<220> FEATURE:
<223> OTHER INFORMATION: primer

<400> SEQUENCE: 1
cggggtacca taacttcgta taatgtatgc tatacgaagt tattcgacca agagatgata     60
actgttac                                                             68

<210> SEQ ID NO 2
<211> LENGTH: 37
<212> TYPE: DNA
<213> ORGANISM: Artificial Sequence
<220> FEATURE:
<223> OTHER INFORMATION: primer

<400> SEQUENCE: 2
catttctaca aaaaaagctc caaggcaaca aattgac                              37

<210> SEQ ID NO 3
<211> LENGTH: 38
<212> TYPE: DNA
<213> ORGANISM: Artificial Sequence
<220> FEATURE:
<223> OTHER INFORMATION: primer

<400> SEQUENCE: 3
tgttgccttg gagcttttt tgtagaaatg tcttggtg                              38

<210> SEQ ID NO 4
<211> LENGTH: 50
<212> TYPE: DNA
<213> ORGANISM: Artificial Sequence
<220> FEATURE:
<223> OTHER INFORMATION: primer

<400> SEQUENCE: 4
ctcgagggat ccgcggccgc acgcgttgtg ttttgatagt tgttcaattg                50

<210> SEQ ID NO 5
<211> LENGTH: 47
<212> TYPE: DNA
<213> ORGANISM: Artificial Sequence
<220> FEATURE:
<223> OTHER INFORMATION: primer

<400> SEQUENCE: 5
acgcgtgcgg ccgcggatcc ctcgagaccg gttaacatca tggcatg                   47

<210> SEQ ID NO 6
<211> LENGTH: 70
<212> TYPE: DNA
<213> ORGANISM: Artificial Sequence
<220> FEATURE:
<223> OTHER INFORMATION: primer

<400> SEQUENCE: 6
ggcaattcca tatgataact tcgtatagca tacattatac gaagttatct gcaggactcg     60
aacctgcgcg                                                           70

<210> SEQ ID NO 7
<211> LENGTH: 36
<212> TYPE: DNA
<213> ORGANISM: Artificial Sequence
<220> FEATURE:
<223> OTHER INFORMATION: primer

<400> SEQUENCE: 7
cggggtaccg aattcgacga aagggcctcg tgatac                        36

<210> SEQ ID NO 8
<211> LENGTH: 42
<212> TYPE: DNA
<213> ORGANISM: Artificial Sequence
<220> FEATURE:
<223> OTHER INFORMATION: primer

<400> SEQUENCE: 8
ggaattccat atgcctgcag ggcctggggt gcctaatgag tg                 42

<210> SEQ ID NO 9
<211> LENGTH: 39
<212> TYPE: DNA
<213> ORGANISM: Artificial Sequence
<220> FEATURE:
<223> OTHER INFORMATION: primer

<400> SEQUENCE: 9
ccggaattcc ccgggcagcc ttaaagagcc cgctaaaag                     39

<210> SEQ ID NO 10
<211> LENGTH: 29
<212> TYPE: DNA
<213> ORGANISM: Artificial Sequence
<220> FEATURE:
<223> OTHER INFORMATION: primer

<400> SEQUENCE: 10
cggggtaccg gctgatgata tttgctacg                                29

<210> SEQ ID NO 11
<211> LENGTH: 33
<212> TYPE: DNA
<213> ORGANISM: Artificial Sequence
<220> FEATURE:
<223> OTHER INFORMATION: primer

<400> SEQUENCE: 11
ggaattccat atgagaaagc tagagtaaaa tag                           33

<210> SEQ ID NO 12
<211> LENGTH: 39
<212> TYPE: DNA
<213> ORGANISM: Artificial Sequence
<220> FEATURE:
<223> OTHER INFORMATION: primer

<400> SEQUENCE: 12
catgcctgca ggcccgggaa ttccttgtgg aagatcttg                     39

<210> SEQ ID NO 13
<211> LENGTH: 29
<212> TYPE: DNA
<213> ORGANISM: Artificial Sequence
<220> FEATURE:
<223> OTHER INFORMATION: primer

<400> SEQUENCE: 13
gcgacgcgta tggcgaaggc agatggcag                                              29

<210> SEQ ID NO 14
<211> LENGTH: 30
<212> TYPE: DNA
<213> ORGANISM: Artificial Sequence
<220> FEATURE:
<223> OTHER INFORMATION: primer

<400> SEQUENCE: 14
ccgctcgagt tagtccttcc aacttccttc                                             30

<210> SEQ ID NO 15
<211> LENGTH: 30
<212> TYPE: DNA
<213> ORGANISM: Artificial Sequence
<220> FEATURE:
<223> OTHER INFORMATION: primer

<400> SEQUENCE: 15
cggggtacct tttttgtaga aatgtcttgg                                             30

<210> SEQ ID NO 16
<211> LENGTH: 50
<212> TYPE: DNA
<213> ORGANISM: Artificial Sequence
<220> FEATURE:
<223> OTHER INFORMATION: primer

<400> SEQUENCE: 16
ctcgagggat ccgcggccgc acgcgttgtg ttttgatagt tgttcaattg                       50

<210> SEQ ID NO 17
<211> LENGTH: 47
<212> TYPE: DNA
<213> ORGANISM: Artificial Sequence
<220> FEATURE:
<223> OTHER INFORMATION: primer

<400> SEQUENCE: 17
acgcgtgcgg ccgcggatcc ctcgagaccg gttaacatca tggcatg                          47

<210> SEQ ID NO 18
<211> LENGTH: 35
<212> TYPE: DNA
<213> ORGANISM: Artificial Sequence
<220> FEATURE:
<223> OTHER INFORMATION: primer

<400> SEQUENCE: 18
ttggatgtta gatctctgca ggactcgaac ctgcg                                       35

<210> SEQ ID NO 19
<211> LENGTH: 35
<212> TYPE: DNA
<213> ORGANISM: Artificial Sequence
<220> FEATURE:
<223> OTHER INFORMATION: primer

<400> SEQUENCE: 19
gttcgagtcc tgcagagatc taacatccaa agacg                                       35

<210> SEQ ID NO 20
<211> LENGTH: 36

<212> TYPE: DNA
<213> ORGANISM: Artificial Sequence
<220> FEATURE:
<223> OTHER INFORMATION: primer

<400> SEQUENCE: 20
gtatcggctt accatctcgt ttcgaataat tagttg        36

<210> SEQ ID NO 21
<211> LENGTH: 36
<212> TYPE: DNA
<213> ORGANISM: Artificial Sequence
<220> FEATURE:
<223> OTHER INFORMATION: primer

<400> SEQUENCE: 21
attattcgaa acgagatggt aagccgatac gtaccc        36

<210> SEQ ID NO 22
<211> LENGTH: 36
<212> TYPE: DNA
<213> ORGANISM: Artificial Sequence
<220> FEATURE:
<223> OTHER INFORMATION: primer

<400> SEQUENCE: 22
tctaaggcta caaacctacc caatcagtac gttaat        36

<210> SEQ ID NO 23
<211> LENGTH: 36
<212> TYPE: DNA
<213> ORGANISM: Artificial Sequence
<220> FEATURE:
<223> OTHER INFORMATION: primer

<400> SEQUENCE: 23
gtactgattg ggtaggtttg tagccttaga catgac        36

<210> SEQ ID NO 24
<211> LENGTH: 34
<212> TYPE: DNA
<213> ORGANISM: Artificial Sequence
<220> FEATURE:
<223> OTHER INFORMATION: primer

<400> SEQUENCE: 24
ggaattccat atgggatccg cacaaacgaa ggtc        34

<210> SEQ ID NO 25
<211> LENGTH: 31
<212> TYPE: DNA
<213> ORGANISM: Artificial Sequence
<220> FEATURE:
<223> OTHER INFORMATION: primer

<400> SEQUENCE: 25
ccggaattct cgaacatagt ccgtccccgg g        31

<210> SEQ ID NO 26
<211> LENGTH: 36
<212> TYPE: DNA
<213> ORGANISM: Artificial Sequence
<220> FEATURE:
<223> OTHER INFORMATION: primer

<400> SEQUENCE: 26
ggacgaggca agctttcgat gtcgactcaa cctatc                                36

<210> SEQ ID NO 27
<211> LENGTH: 31
<212> TYPE: DNA
<213> ORGANISM: Artificial Sequence
<220> FEATURE:
<223> OTHER INFORMATION: primer

<400> SEQUENCE: 27
ttgagtcgac atcgaaagct tgcctcgtcc c                                     31

<210> SEQ ID NO 28
<211> LENGTH: 29
<212> TYPE: DNA
<213> ORGANISM: Artificial Sequence
<220> FEATURE:
<223> OTHER INFORMATION: primer

<400> SEQUENCE: 28
cggggtaccg tcgacactgg atggcggcg                                        29

<210> SEQ ID NO 29
<211> LENGTH: 40
<212> TYPE: DNA
<213> ORGANISM: Artificial Sequence
<220> FEATURE:
<223> OTHER INFORMATION: primer

<400> SEQUENCE: 29
aaggaaaaaa gcggccgcat gtccaattta ctgaccgtac                            40

<210> SEQ ID NO 30
<211> LENGTH: 30
<212> TYPE: DNA
<213> ORGANISM: Artificial Sequence
<220> FEATURE:
<223> OTHER INFORMATION: primer

<400> SEQUENCE: 30
ccgctcgagc taatcgccat cttccagcag                                       30

<210> SEQ ID NO 31
<211> LENGTH: 34
<212> TYPE: DNA
<213> ORGANISM: Artificial Sequence
<220> FEATURE:
<223> OTHER INFORMATION: primer

<400> SEQUENCE: 31
ataacttcgt ataatgtatg ctatacgaag ttat                                  34

<210> SEQ ID NO 32
<211> LENGTH: 23
<212> TYPE: DNA
<213> ORGANISM: Artificial Sequence
<220> FEATURE:
<223> OTHER INFORMATION: primer

<400> SEQUENCE: 32
gttcataaca tacaaatttt atg                                              23

<210> SEQ ID NO 33
<211> LENGTH: 22
<212> TYPE: DNA
<213> ORGANISM: Artificial Sequence

```
<220> FEATURE:
<223> OTHER INFORMATION: primer

<400> SEQUENCE: 33
gagatgtttt catcgtgttc ac                                              22

<210> SEQ ID NO 34
<211> LENGTH: 21
<212> TYPE: DNA
<213> ORGANISM: Artificial Sequence
<220> FEATURE:
<223> OTHER INFORMATION: primer

<400> SEQUENCE: 34
tgtaattcat tggggaggat g                                               21

<210> SEQ ID NO 35
<211> LENGTH: 23
<212> TYPE: DNA
<213> ORGANISM: Artificial Sequence
<220> FEATURE:
<223> OTHER INFORMATION: primer

<400> SEQUENCE: 35
ggaaagcgag attccaagtc atc                                             23

<210> SEQ ID NO 36
<211> LENGTH: 30
<212> TYPE: DNA
<213> ORGANISM: Artificial Sequence
<220> FEATURE:
<223> OTHER INFORMATION: primer

<400> SEQUENCE: 36
cgacgcgtat gtcgaatcaa gaagaaggac                                      30

<210> SEQ ID NO 37
<211> LENGTH: 31
<212> TYPE: DNA
<213> ORGANISM: Artificial Sequence
<220> FEATURE:
<223> OTHER INFORMATION: primer

<400> SEQUENCE: 37
ccgctcgagt caagactcta gcttttcatt c                                    31

<210> SEQ ID NO 38
<211> LENGTH: 49
<212> TYPE: DNA
<213> ORGANISM: Artificial Sequence
<220> FEATURE:
<223> OTHER INFORMATION: primer

<400> SEQUENCE: 38
ccgctcgaga aagagaggc tgaagctcac ccagaaacgc tggtgaaag                  49

<210> SEQ ID NO 39
<211> LENGTH: 40
<212> TYPE: DNA
<213> ORGANISM: Artificial Sequence
<220> FEATURE:
<223> OTHER INFORMATION: primer

<400> SEQUENCE: 39
aaggaaaaaa gcggccgctt accaatgctt aatcagtgag                           40
```

<210> SEQ ID NO 40
<211> LENGTH: 65
<212> TYPE: DNA
<213> ORGANISM: Artificial Sequence
<220> FEATURE:
<223> OTHER INFORMATION: primer

<400> SEQUENCE: 40
cggggtacca taacttcgta taatgtatgc tatacgaagt tatcttttgt tgtttccggg    60
tgtac                                                                65

<210> SEQ ID NO 41
<211> LENGTH: 36
<212> TYPE: DNA
<213> ORGANISM: Artificial Sequence
<220> FEATURE:
<223> OTHER INFORMATION: primer

<400> SEQUENCE: 41
tgaaggaaat ctcattgtat atgagatagt tgattg                              36

<210> SEQ ID NO 42
<211> LENGTH: 38
<212> TYPE: DNA
<213> ORGANISM: Artificial Sequence
<220> FEATURE:
<223> OTHER INFORMATION: primer

<400> SEQUENCE: 42
actatctcat atacaatgag atttccttca atttttac                            38

<210> SEQ ID NO 43
<211> LENGTH: 37
<212> TYPE: DNA
<213> ORGANISM: Artificial Sequence
<220> FEATURE:
<223> OTHER INFORMATION: primer

<400> SEQUENCE: 43
tcataagaaa ttcgcttacc aatgcttaat cagtgag                             37

<210> SEQ ID NO 44
<211> LENGTH: 36
<212> TYPE: DNA
<213> ORGANISM: Artificial Sequence
<220> FEATURE:
<223> OTHER INFORMATION: primer

<400> SEQUENCE: 44
attaagcatt ggtaagcgaa tttcttatga tttatg                              36

<210> SEQ ID NO 45
<211> LENGTH: 36
<212> TYPE: DNA
<213> ORGANISM: Artificial Sequence
<220> FEATURE:
<223> OTHER INFORMATION: primer

<400> SEQUENCE: 45
gctatggtgt gtgggaccgg gcccgacgtc gcatgc                              36

<210> SEQ ID NO 46
<211> LENGTH: 39
<212> TYPE: DNA
<213> ORGANISM: Artificial Sequence
<220> FEATURE:
<223> OTHER INFORMATION: primer

<400> SEQUENCE: 46
gacgtcgggc ccggtcccac acaccatagc ttcaaaatg                              39

<210> SEQ ID NO 47
<211> LENGTH: 31
<212> TYPE: DNA
<213> ORGANISM: Artificial Sequence
<220> FEATURE:
<223> OTHER INFORMATION: primer

<400> SEQUENCE: 47
cccaagctta gcttgcaaat taaagccttc g                                      31

<210> SEQ ID NO 48
<211> LENGTH: 30
<212> TYPE: DNA
<213> ORGANISM: Artificial Sequence
<220> FEATURE:
<223> OTHER INFORMATION: primer

<400> SEQUENCE: 48
cccaagcttt tttttgtaga aatgtcttgg                                        30

<210> SEQ ID NO 49
<211> LENGTH: 70
<212> TYPE: DNA
<213> ORGANISM: Artificial Sequence
<220> FEATURE:
<223> OTHER INFORMATION: primer

<400> SEQUENCE: 49
ggcaattcca tatgataact tcgtatagca tacattatac gaagttatct gcaggactcg       60
aacctgcgcg                                                              70

<210> SEQ ID NO 50
<211> LENGTH: 33
<212> TYPE: DNA
<213> ORGANISM: Artificial Sequence
<220> FEATURE:
<223> OTHER INFORMATION: primer

<400> SEQUENCE: 50
ccggaattcc agctgccctc acggtggtta cgg                                    33

<210> SEQ ID NO 51
<211> LENGTH: 32
<212> TYPE: DNA
<213> ORGANISM: Artificial Sequence
<220> FEATURE:
<223> OTHER INFORMATION: primer

<400> SEQUENCE: 51
cggggtaccc atctgattgg ttgagctctt tg                                     32

<210> SEQ ID NO 52
<211> LENGTH: 34
<212> TYPE: DNA
<213> ORGANISM: Artificial Sequence
<220> FEATURE:
<223> OTHER INFORMATION: primer

<400> SEQUENCE: 52
gcaattccat atgggggcct tggctggttt cctc    34

<210> SEQ ID NO 53
<211> LENGTH: 35
<212> TYPE: DNA
<213> ORGANISM: Artificial Sequence
<220> FEATURE:
<223> OTHER INFORMATION: primer

<400> SEQUENCE: 53
aacctgcagg cagctgtacc ggtttacaga aggac    35

<210> SEQ ID NO 54
<211> LENGTH: 21
<212> TYPE: DNA
<213> ORGANISM: Artificial Sequence
<220> FEATURE:
<223> OTHER INFORMATION: primer

<400> SEQUENCE: 54
atcgactctc tcaatgaact c    21

<210> SEQ ID NO 55
<211> LENGTH: 21
<212> TYPE: DNA
<213> ORGANISM: Artificial Sequence
<220> FEATURE:
<223> OTHER INFORMATION: primer

<400> SEQUENCE: 55
ctaaatctga gtaaccgatg a    21

<210> SEQ ID NO 56
<211> LENGTH: 21
<212> TYPE: DNA
<213> ORGANISM: Artificial Sequence
<220> FEATURE:
<223> OTHER INFORMATION: primer

<400> SEQUENCE: 56
tgtaattcat tggggaggat g    21

<210> SEQ ID NO 57
<211> LENGTH: 21
<212> TYPE: DNA
<213> ORGANISM: Artificial Sequence
<220> FEATURE:
<223> OTHER INFORMATION: primer

<400> SEQUENCE: 57
gcacagtatc gggatacaaa g    21

<210> SEQ ID NO 58
<211> LENGTH: 3669
<212> TYPE: DNA
<213> ORGANISM: Pichia pastoris

<400> SEQUENCE: 58
tgagccggcc agtaaccgtc ttggagctgt tcataagag tcattaggga tcaataacgt    60
tctaatctgt tcataacata caaattttat ggctgcatag ggaaaaattc tcaacagggt    120
agccgaatga ccctgatata gacctgcgac accatcatac ccatagatct gcctgacagc    180
cttaaagagc ccgctaaaag acccggaaaa ccgagagaac tctggattag cagtctgaaa    240
aagaatcttc actctgtcta gtggagcaat taatgtctta gcggcacttc ctgctactcc    300

```
gccagctact cctgaataga tcacatactg caaagactgc ttgtcgatga ccttggggtt    360
atttagcttc aagggcaatt tttgggacat tttggcacac ggagactcag aaacagacac    420
agagcgttct gagtcctggt gctcctgacg taggcctaga acaggaatta ttggctttat    480
ttgtttgtcc atttcatagg cttggggtaa tagatagatg acagagaaat agagaagacc    540 taatatttt tgttcatggc aaatcgcggg ttcgcggtcg ggtcacacac ggagaagtaa     600
tgagaagagc tggtaatctg gggtaaaagg gttcaaaaga aggtcgcctg gtagggatgc    660
aatacaaggt tgtcttggag tttacattga ccagatgatt tggcttttc tctgttcaat     720 tcacattttt cagcgagaat cggattgacg agaaatggc ggggtgtggg gtggatagat     780
ggcagaaatg ctcgcaatca ccgcgaaaga aagactttat ggaatagaac tactgggtgg    840
tgtaaggatt acatagctag tccaatggag tccgttggaa aggtaagaag aagctaaaac    900
cggctaagta actagggaag aatgatcaga ctttgatttg atgaggtctg aaaatactct    960
gctgcttttt cagttgcttt ttccctgcaa cctatcattt tccttttcat aagcctgcct   1020
tttctgtttt cacttatatg agttccgccg agacttcccc aaattctctc ctggaacatt   1080
ctctatcgct ctccttccaa gttgcgcccc ctggcactgc ctagtaatat taccacgcga   1140
cttatattca gttccacaat ttccagtgtt cgtagcaaat atcatcagcc atggcgaagg   1200
cagatggcag tttgctctac tataatcctc acaatccacc cagaaggtat tacttctaca   1260
tggctatatt cgccgtttct gtcatttgcg ttttgtacgg accctcacaa caattatcat   1320
ctccaaaaat agactatgat ccattgacgc tccgatcact tgatttgaag actttggaag   1380
ctccttcaca gttgagtcca ggcaccgtag aagataatct tcgaagacaa ttggagtttc   1440
attttcctta ccgcagttac gaaccttttc cccaacatat ttggcaaacg tggaaagttt   1500
ctccctctga tagttccttt ccgaaaaact tcaaagactt aggtgaaagt tggctgcaaa   1560
ggtccccaaa ttatgatcat tttgtgatac ccgatgatgc agcatgggaa cttattcacc   1620
atgaatacga acgtgtacca gaagtcttgg aagctttcca cctgctacca gagcccattc   1680
taaaggccga ttttttcagg tatttgattc tttttgcccg tggaggactg tatgctgaca   1740
tggacactat gttattaaaa ccaatagaat cgtggctgac tttcaatgaa actattggtg   1800
gagtaaaaaa caatgctggg ttggtcattg gtattgaggc tgatcctgat agacctgatt   1860
ggcacgactg gtatgctaga aggatacaat tttgccaatg gcaattcag tccaaacgag    1920 gacacccagc actgcgtgaa ctgattgtaa gagttgtcag cacgacttta cggaaagaga   1980
aaagcggtta cttgaacatg gtggaaggaa aggatcgtgg aagtgatgtg atggactgga   2040
cgggtccagg aatatttaca gacactctat ttgattatat gactaatgtc aatacaacag   2100
gccactcagg ccaaggaatt ggagctggct cagcgtatta caatgcctta tcgttggaag   2160
aacgtgatgc cctctctgcc cgcccgaacg gagagatgtt aaaagagaaa gtcccaggta   2220
aatatgcaca gcaggttgtt ttatgggaac aatttaccaa cctgcgctcc cccaaattaa   2280
tcgacgatat tcttattctt ccgatcacca gcttcagtcc agggattggc cacagtggag   2340
ctggagattt gaaccatcac cttgcatata ttaggcatac atttgaagga agttggaagg   2400
actaaagaaa gctagagtaa aatagatata gcgagattag agaatgaata ccttcttcta   2460
agcgatcgtc cgtcatcata gaatatcatg gactgtatag ttttttttt gtacatataa    2520 tgattaaacg gtcatccaac atctcgttga cagatctctc agtacgcgaa atccctgact   2580
atcaaagcaa gaaccgatga agaaaaaaac aacagtaacc caaacaccac aacaaacact   2640
```

-continued

| | |
|---|---|
| ttatcttctc cccccaaca ccaatcatca aagagatgtc ggaaccaaac accaagaagc | 2700 |
| aaaaactaac cccatataaa aacatcctgg tagataatgc tggtaacccg ctctccttcc | 2760 |
| atattctggg ctacttcacg aagtctgacc ggtctcagtt gatcaacatg atcctcgaaa | 2820 |
| tgggtggcaa gatcgttcca gacctgcctc ctctggtaga tggagtgttg ttttgacag | 2880 |
| gggattacaa gtctattgat gaagataccc taaagcaact gggggacgtt ccaatataca | 2940 |
| gagactcctt catctaccag tgttttgtgc acaagacatc tcttcccatt gacactttcc | 3000 |
| gaattgacaa gaacgtcgac ttggctcaag atttgatcaa tagggcccctt caagagtctg | 3060 |
| tggatcatgt cacttctgcc agcacagctg cagctgctgc tgttgttgtc gctaccaacg | 3120 |
| gcctgtcttc taaaccagac gctcgtacta gcaaaataca gttcactccc gaagaagatc | 3180 |
| gttttattct tgactttgtt aggagaaatc ctaaacgaag aaacacacat caactgtaca | 3240 |
| ctgagctcgc tcagcacatg aaaaaccata cgaatcattc tatccgccac agatttcgtc | 3300 |
| gtaatctttc cgctcaactt gattgggttt atgatatcga tccattgacc aaccaacctc | 3360 |
| gaaaagatga aaacgggaac tacatcaagg tacaagatct tccacaagga attcgtggtc | 3420 |
| attattctgc ccaagatgat tacaatttgt gtttatcggt tcaacctttc attgaatctg | 3480 |
| tagatgagac aacaggccaa gaattttca aacctctgaa aggtgtattt gatgacttgg | 3540 |
| aatctcgctt tcctcaccat acaaagactt cctggagaga cagattcaga aagtttgcct | 3600 |
| ctaaatacgg tgttcgtcag tacatcgcgt attatgaaaa gactgttgaa ctcaatggtg | 3660 |
| ttcctaatc | 3669 |

<210> SEQ ID NO 59
<211> LENGTH: 1431
<212> TYPE: DNA
<213> ORGANISM: Artificial Sequence
<220> FEATURE:
<223> OTHER INFORMATION: kanMX module

<400> SEQUENCE: 59

| | |
|---|---|
| aagcttgcct cgtccccgcc gggtcacccg gccagcgaca tggaggccca gaataccctc | 60 |
| cttgacagtc ttgacgtgcg cagctcaggg gcatgatgtg actgtcgccc gtacatttag | 120 |
| cccatacatc cccatgtata atcatttgca tccatacatt ttgatggccg cacggcgcga | 180 |
| agcaaaaatt acggctcctc gctgcagacc tgcgagcagg gaaacgctcc cctcacagac | 240 |
| gcgttgaatt gtccccacgc cgcgcccctg tagagaaata taaaaggtta ggatttgcca | 300 |
| ctgaggttct tctttcatat acttcctttt aaaatcttgc taggatacag ttctcacatc | 360 |
| acatccgaac ataaacaacc atgggtaagg aaaagactca cgtttcgagg ccgcgattaa | 420 |
| attccaacat ggatgctgat ttatatgggt ataaatgggc tcgcgataat gtcgggcaat | 480 |
| caggtgcgac aatctatcga ttgtatggga gcccgatgc gccagagttg tttctgaaac | 540 |
| atggcaaagg tagcgttgcc aatgatgtta cagatgagat ggtcagacta aactggctga | 600 |
| cggaatttat gcctcttccg accatcaagc atttatccg tactcctgat gatgcatggt | 660 |
| tactcaccac tgcgatcccc ggcaaaacag cattccaggt attagaagaa tatcctgatt | 720 |
| caggtgaaaa tattgttgat gcgctggcag tgttcctgcg ccggttgcat tcgattcctg | 780 |
| tttgtaattg tccttttaac agcgatcgcg tatttcgtct cgctcaggcg caatcacgaa | 840 |
| tgaataacgg tttggttgat gcgagtgatt ttgatgacga gcgtaatggc tggcctgttg | 900 |
| aacaagtctg gaaagaaatg cataagcttt tgccattctc accggattca gtcgtcactc | 960 |
| atggtgattt ctcacttgat aaccttattt ttgacgaggg gaaattaata ggttgtattg | 1020 |

| | | | |
|---|---|---|---|
| atgttggacg | agtcggaatc | gcagaccgat | accaggatct tgccatccta tggaactgcc | 1080 |
| tcggtgagtt | ttctccttca | ttacagaaac | ggcttttttca aaaatatggt attgataatc | 1140 |
| ctgatatgaa | taaattgcag | tttcatttga | tgctcgatga gttttttctaa tcagtactga | 1200 |
| caataaaaag | attcttgttt | tcaagaactt | gtcattgtta tagttttttt atattgtagt | 1260 |
| tgttctattt | taatcaaatg | ttagcgtgat | ttatattttt tttcgcctcg acatcatctg | 1320 |
| cccagatgcg | aagttaagtg | cgcagaaagt | aatatcatgc gtcaatcgta tgtgaatgct | 1380 |
| ggtcgctata | ctgctgtcga | ttcgatacta | acgccgccat ccagtgtcga c | 1431 |

<210> SEQ ID NO 60
<211> LENGTH: 2668
<212> TYPE: DNA
<213> ORGANISM: Pichia pastoris

<400> SEQUENCE: 60

| | | | | |
|---|---|---|---|---|
| acgaaaactg | tcaaatatgt | agttaatgac | cctgttgccg gtcccttggt caaacaattg | 60 |
| aacccaggtt | ttgcagcacc | agaactcccg | ttcaagagaa tggagtacgt agaagcactg | 120 |
| aaatggctta | atgatcacag | tattccaaac | gaagaaggac aacctttcaa atttggtgac | 180 |
| gacattgccg | aggctgctga | gagaaagatg | accgatacta ttggtgttcc aattcttttg | 240 |
| actcgtttcc | cacttgaaat | taagtcattt | tacatgaaac gttgcgccga cgatccaaga | 300 |
| gttactgaat | ctgtagatgt | gctgatgcca | actgttggag aaatcaccgg tggctctatg | 360 |
| aggatcgact | ctctcaatga | actcctggaa | ggttttgaac gtgaaaagct tgacaaaagt | 420 |
| gcgtactact | ggttcattga | tcaacgaaaa | tatggtacct gccctcacgg tggttacggt | 480 |
| ctaggaacgg | aacgtatctt | agcatggttg | tgcgacagat tcactgtgaa agactgttca | 540 |
| ttatacccac | gtttcactgg | gagatgtaag | ccttaggtgt tttaccctga ttagataata | 600 |
| caataaccaa | cagaaatacg | agaatctaaa | ctaatttcga tgattcattt ttcttttttac | 660 |
| cgcgctgcct | cttttggcaa | ttctttcacc | tatattctac cttctctttc cttttgttct | 720 |
| aaacttatta | ccagctatct | atgtcgaatc | aagaagaagg acttaaactg tggggtggca | 780 |
| ggtttactgg | ggctactgac | cccttgatgg | atttgtataa cgcttcctta ccttacgaca | 840 |
| agaaaatgta | caaggtggat | ttagaaggaa | caaaagtta cactgagggc ctggagaaaa | 900 |
| ttaatttgct | aactaaagac | gaactaagtg | agattcatcg tggtctcaaa ttgattgaag | 960 |
| cagagtgggc | agaagggaag | tttgttgaga | agccagggga tgaggatatt cacactgcta | 1020 |
| atgaacgtcg | cttgggtgag | ttgattggtc | gtggaatctc tggtaaggtt cataccggaa | 1080 |
| ggtctagaaa | tgatcaagtt | gccactgata | tgcggttgta tgtcagagac aatctaactc | 1140 |
| agttggctga | ctatctgaag | cagttcattc | aagtaatcat caagagagct gaacaggaaa | 1200 |
| tagacgtctt | gatgcccggt | tatactcact | gcaaagagc tcaaccaatc agatggtctc | 1260 |
| actggttgag | catgtatgct | acctatttca | ctgaagatta tgagactg aatcaaatcg | 1320 |
| ttaaaaggtt | gaacaaatcc | ccattgggag | ctggagcttt ggctggtcat ccttatggaa | 1380 |
| ttgatcgtga | atacattgct | gagagattag | ggtttgattc tgttattggt aattctttgg | 1440 |
| ccgctgtttc | agacagagat | tttgtagtcg | aaaccatgtt ctggtcttcg ttgttttatga | 1500 |
| atcatatttc | tcgattctca | gaagatttga | tcatttactc cactggagag tttggattta | 1560 |
| tcaagttggc | agatgcttat | tctactggat | cttctctgat gcctacaaaa aaaaacccag | 1620 |
| actcttttgga | gttattgagg | ggtaaatctg | gtagatgttt tgggcccttg gctggtttcc | 1680 |

-continued

```
tcatgtctat taagtccatt ccgtcaacct ataacaaaga tatgcaagag gataaggagc    1740
ctttatttga tactctaatc actgtagagc actcgatttt gatagcatcc ggtgtagttt    1800
ctaccttgaa cattgatgcc gaacgaatga agaatgctct aactatggat atgctggcta    1860
cagatcttgc cgactattta gttagaaggg gagttccatt cagagaaact caccacattt    1920
ctggtgaatg tgtcagacaa gccgaggagt tgaacctttc tggtattgat cagttgtccc    1980
tcgaacaatt gaaatccatt gactcccgtt ttgaggctga tgtggcttca acgtttgact    2040
ttgaagccag tgttgaaaaa agaactgcca ccggaggaac ttctaagact gctgttttaa    2100
agcaattgga tgcactgaat gaaaagctag agtcttgaag gttttatact gagtttgtta    2160
atgatacaat aaactgttat agtacataca attgaaactc tcttatctat actggggac     2220 cttctcgcag aatggtataa atatctacta actgactgtc gtacggccta ggggtctctt    2280
cttcgattat ttgcaggtcg gaacatcctt cgtctgatgc ggatctcctg agacaaagtt    2340
cacgggtatc tagtattcta tcagcataaa tggaggacct ttctaaacta aactttgaat    2400
cgtctccagc agcatcctcg cataatcctt ttgtcatttc ctctatgtct attgtcactg    2460
tggttggcgc atcaagagtc gtccttctgt aaaccggtac agaattccta ccactagaag    2520
cttgaaatgg ggagggtttc agctttgtat cccgatactg tgctttaaaa agggagtcca    2580
aactgaaatc ttttcggaa tcattggatg atacctctgt attagatctc ctatgtatcg     2640
gtttcctcgg gtagatagaa ctgtcgac                                        2668
```

<210> SEQ ID NO 61
<211> LENGTH: 336
<212> TYPE: DNA
<213> ORGANISM: Escherichia coli

<400> SEQUENCE: 61

```
atggtaagcc gatacgtacc cgatatgggc gatctgatt gggttgattt tgacccgaca      60
aaaggtagcg agcaagctgg acatcgtcca gctgttgtcc tgagtccttt catgtacaac    120
aacaaaacag gtatgtgtct gtgtgttcct tgtacaacgc aatcaaaagg atatccgttc    180
gaagttgttt tatccggtca ggaacgtgat ggcgtagcgt tagctgatca ggtaaaaagt    240
atcgcctggc gggcaagagg agcaacgaag aaaggaacag ttgccccaga ggaattacaa    300
ctcattaaag ccaaaattaa cgtactgatt gggtag                              336
```